US012702445B2

(12) United States Patent
Cominotto et al.

(10) Patent No.: US 12,702,445 B2
(45) Date of Patent: Aug. 11, 2026

(54) PROGRAMMABLE TOOL FOR EXTERNAL FIXATION STRUT ADJUSTMENT

(71) Applicants: ORTHOFIX S.R.L., Bussolengo (IT); Texas Scottish Rite Hospital for Children, Dallas, TX (US)

(72) Inventors: Andrea Forcolin Cominotto, Padua (IT); Nicola Gaburro, Caselle di Sommacampagna (IT); John David Ross, Jr., Ovilla, TX (US); Karen Divita Standefer, Flower Mound, TX (US); Mikhail Samchukov, Coppell, TX (US); Alexander Cherkashin, Flower Mound, TX (US)

(73) Assignees: Orthofix S.R.L., Bussolengo (IT); Texas Scottish Rite Hospital for Children, Dallas, TX (US)

( * ) Notice: Subject to any disclaimer, the term of this patent is extended or adjusted under 35 U.S.C. 154(b) by 85 days.

(21) Appl. No.: 18/390,972

(22) Filed: Dec. 20, 2023

(65) Prior Publication Data

US 2024/0206914 A1 Jun. 27, 2024

Related U.S. Application Data

(60) Provisional application No. 63/477,059, filed on Dec. 23, 2022.

(51) Int. Cl.

*A61B 17/66* (2006.01)
*A61B 17/64* (2006.01)

(Continued)

(52) U.S. Cl.

CPC .............. *A61B 17/66* (2013.01); *A61B 17/64* (2013.01); *A61B 17/8875* (2013.01);

(Continued)

(58) Field of Classification Search

CPC .............. A61B 17/62–64; A61B 17/66; A61B 17/8875; A61B 2034/108;

(Continued)

(56) References Cited

U.S. PATENT DOCUMENTS 10,082,384 B1 * 9/2018 Singh .................... A61B 34/10
2011/0004199 A1 * 1/2011 Ross ...................... A61B 90/98 606/1

(Continued)

*Primary Examiner* — Julianna N Harvey

(74) *Attorney, Agent, or Firm* — Haynes and Boone, LLP

(57) ABSTRACT

A tool for adjusting an external fixation strut includes a first connecting portion adapted to perform data communication with the external fixation strut via a connecting portion, and a controller which includes command instructions. Based on the command instructions, the controller is configured to download prescription data including instructions for performing an adjustment of the external fixation strut of the patient, after the tool has been coupled with the external fixation strut, recognize a coupling state with the external fixation strut. Once the coupling is complete and data with the external fixation strut have been exchanged, wait for a date and/or time in which the prescribed adjustment is to be applied based on the prescription data. A related external fixation strut and a related medical assembly are also disclosed.

19 Claims, 19 Drawing Sheets

(51) Int. Cl.
*A61B 17/88* (2006.01)
*B25B 21/00* (2006.01)
*A61B 17/00* (2006.01)
*A61B 90/00* (2016.01)

(52) U.S. Cl.
CPC .... *B25B 21/00* (2013.01); *A61B 2017/00022* (2013.01); *A61B 2090/061* (2016.02)

(58) Field of Classification Search
CPC ..... A61B 17/56–17/7291; B25B 21/00; B25B 23/14
See application file for complete search history.

(56) References Cited

U.S. PATENT DOCUMENTS

| | | | | |
|---|---|---|---|---|
| 2016/0113681 | A1* | 4/2016 | Singh | A61B 17/8875<br>606/104 |
| 2017/0333080 | A1* | 11/2017 | Roschak | A61B 17/7216 |
| 2022/0071662 | A1* | 3/2022 | Heotis | A61B 17/62 |

* cited by examiner

C
215
2120
211
212
200
2120
201
217
213
216
C 218
215
2120
211
222
212
200
2121
214
217
213
216
218

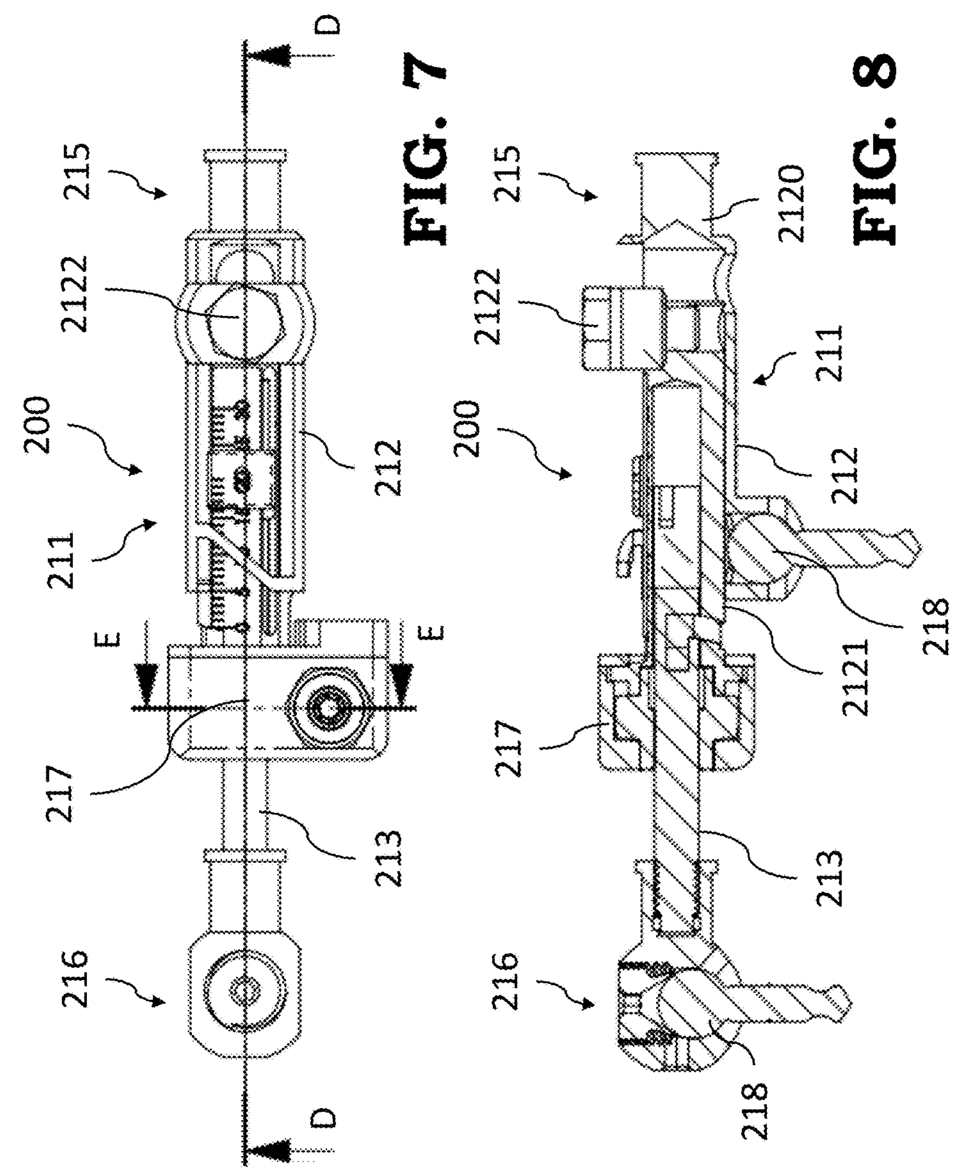
D
215
2122
200
211
212
E
E
217
213
216
D
FIG. 7
215
2120
2122
211
200
212
218
2121
217
213
216
218
FIG. 8
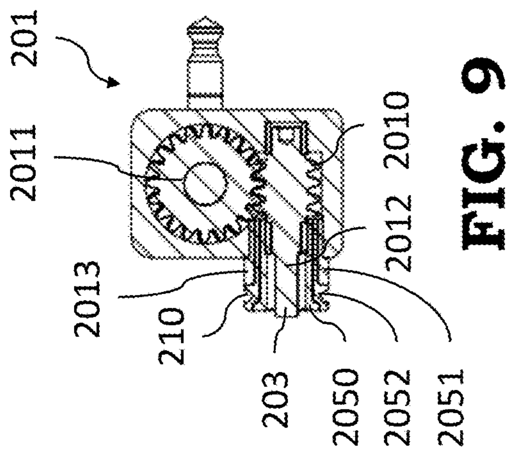
201
2011
2010
2012
2013
210
203
2050
2052
2051
FIG. 9

216
213
200
217
212
2122
215
201
205
211

215
211
212
200
205
213
216
F
F 215
200
211
214
H
G
212
217
2011
213
216

106
111
104
100
102
101
107
109
110
103
105
205
203
216
201
2010
200
215
I 106
111
100
102
104
107
K
109
205
203
2010
2011

J
100
210
2013
216
J 101
1050
108
103
1090
105
1051

PROGRAMMABLE TOOL FOR EXTERNAL FIXATION STRUT ADJUSTMENT

PRIORITY INFORMATION

This patent application claims the benefit of the filing date of U.S. Provisional Patent Application 63/477,059, filed Dec. 23, 2022, entitled, IMPROVED PROGRAMMABLE TOOL FOR EXTERNAL FIXATION STRUT ADJUSTMENT, which is incorporated herein by reference in its entirety.

TECHNICAL FIELD

The present disclosure relates to the field of external fixation, and more specifically to the operation of a tool employed for the incremental or decremental adjustment of struts of an external fixator, particularly during postoperative period. The following description refers to this technical field with the sole purpose to simplify the exposition thereof.

PRIOR ART

Without limiting the scope of the present disclosure, its background is herein described in connection with external fixation devices and related tools for the adjustment of struts or other connection rods thereof.

Generally speaking, external fixation devices are commonly used in a variety of surgical procedures including limb fracture fixation, lengthening and deformity correction. The process involves the application of a rigid framework comprising several rings or arches that are placed externally around the limb and attached to bone segments using wires and half pins inserted into the bone segments and connected to the related section of the external rigid framework.

Rings of the rigid framework located opposite to one another are interconnected by either threaded and/or telescopic struts directly or in conjunction with uniplanar or multiplanar hinges, which allows to adjust position of the rings relative to each other longitudinally, rotationally, horizontally or angularly over a period of time.

For example, in limb lengthening, the bone is surgically divided into two segments and wires and half pins are inserted into bone segments above and below the surgical bone cut and attached to rings of a rigid framework interconnected by struts or telescopic connection struts.

For limb lengthening, the opposite rings are preferably interconnected directly by at least three or four threaded or telescopic struts that are regularly adjusted in length and allowed for gradual separation of bone segments longitudinally.

The rigid framework is used to gradually push the two bone segments apart longitudinally over a period of time (for instance, one millimeter a day). This allows the new bone to gradually form in the gap between bone segments created by this distraction technique. Once the desired amount of lengthening is achieved (e.g., 5-6 cm), the external apparatus is stabilized into a fixed position and left on the bone segments until complete mineralization of the newly formed bone (e.g., 3-6 months, depending on the nature of pathology and/or amount of lengthening).

Similarly, in deformity correction, the bone is surgically divided (usually at the apex of the deformity) into two segments and wires and half pins are inserted into bone segments above and below the surgical bone cut and attached to rings of a rigid framework. In this case also opposite rings of the rigid framework are connected together by threaded struts with attached hinges and angular distractor that is used to gradually push the two bone segments apart angularly over a period of time.

One common fixation device is a circular metal structure known as the Ilizarov apparatus. The Ilizarov apparatus, when used for limb lengthening or deformity correction, consists of several rings or arches that are placed externally around the limb and attached to surgically separated bone segments using wires and half pins. For angular deformity correction, the opposite rings of the Ilizarov apparatus are connected by a pair of hinges that provide an axis of rotation for bone segments and an angular distractor that gradually pushes two rings and associated bone segments apart.

Another common external fixation device is known as Taylor Spatial Frame, which is a hexapod-type external fixation device based on a so-called Stewart platform but shares many components and features of the Ilizarov apparatus.

The Taylor Spatial Frame comprises two external fixation rings attached to bone segments by wires and half pins and connected together by six telescopic struts with multi-planar hinges located at both ends of the struts. Each strut may be lengthened or shortened as necessary to either pull two interconnected ring segments towards each other or push them apart.

Other examples of external fixation devices of this kind are commercially known as TrueLok and Sheffield.

Adjustment of strut length allows manipulating with bone segments acutely or gradually in several axes to perform limb lengthening and correct angular, translational and rotational deformities sequentially or simultaneously.

The amount of daily strut length adjustment is usually calculated by a dedicated software. Once the apparatus is attached to the bone segments, numerous parameters such as deformity parameters, frame parameters, mounting parameters and so forth are entered into the software to characterize one ring position relative to another ring and position of bone segments relative to each other and to the rings. After calculation of the total amount of each strut length adjustment, the software provides a tabled instruction (which is referred to as "prescription") on the amount of each strut length adjustment that should be achieved per each increment, including a number identifying the single strut, the amount of adjustment required, and the time scheduled for such adjustment. In most cases of deformity correction, the struts are adjusted in different directions (shortening/lengthening) and in different amounts.

Since the prescription requires several adjustments over time, usually up to four adjustments per day, most of the time these regulations cannot be performed by the surgeon or by a dedicated practitioner. The task of following the prescription is thus entrusted to the patient or to one of their relatives, which do so by turning an adjustment knob on the struts or by turning the nuts of the threaded or telescopic rods with a wrench.

This way of strut length adjustment is time consuming (e.g., due to loosening and retightening of the threaded rod nuts before and after each adjustment), does not provide precise length adjustment (e.g., due to difficulty to monitor small amounts of adjustments) and creates overall frame instability during adjustments (e.g., due to dimensional clearance between connection elements).

Furthermore, the prescription for length adjustments can be complicated, and human errors are prone to occur during the course of a complicated prescription. Even though the patient is invited to verify compliance between prescription and frame status by inspecting the strut length, an error can well remain unnoticed, due to a negligent check or a total lack thereof.

Additionally, it must be considered that the feedback to the surgeon depends on the patient, who is demanded to communicate the adjustments made on the struts, usually by uploading the information on a dedicated portal. Once again, carelessness by the patient may result in incorrect or incomplete information given to the surgeon.

It is easy to understand that errors in carrying out the prescription, particularly if they are not promptly identified by the surgeon, may result in detrimental effects on the final outcome of the correction process.

To alleviate the aforementioned drawbacks, in recent year a programmable tool has been proposed for incrementally adjusting the length of the external fixator strut. The tool, described for instance in prior art application WO 2009/105479 in the name of Texas Scottish Rite Hospital for Children, is designed as an electric wrench meant to engage with the adjustment mechanism of the external fixator struts. The tool has an internal memory for storing the adjustment parameters of the prescription and is set to automatically adjust each of the struts according to said parameters.

Even though it provides numerous advantages over the previously discussed prior art, the programmable tool has however remaining drawbacks, in particularly relating to the ease of use of the device.

Indeed, in order to correctly adjust the length parameters of the struts according to the memorized prescription, it is advisable to feed the tool with real-time measurements of the struts' length. If the tool were to implement the length increments or decrements according to the prescription without feedback, the adjustment process could easily get flawed due to incremental errors, and any erroneous action by the patient—for instance coupling the tool to the wrong strut when applying the prescription—would probably disrupt the correct application of the adjustment plan over time.

Therefore, the programmable tool is preferably provided with means to measure the strut length, for instance a digital ruler which is meant to be coupled to the opposite ends thereof. However, such measurement means add to the complexity of the device, and more importantly they require a positive action by the patient, thus making the process of applying the prescription more difficult and prone to human error.

It is observed that alternative methods of measuring the strut length, for instance through a sensor housed on-board of the strut itself, have been ruled out to date due to the difficulty in powering the internal sensor and communicating the sensor signal to the tool. In particular, wireless methods are difficult to implement due to practical design concerns and regulatory compliance, while the addition of a wired plug appears to be impractical both in terms of product design and usability.

Moreover, the programmable tool preferably requires further interface means, such as means to identify the individual struts, to help the patient in correctly performing the prescription. This means can be for instance an RFID reader meant to read a unique identification code from the strut. However, this adds complexity and leaves a degree of uncertainty in the process since the patient might erroneously omit the step of identifying the strut or else correctly identifying the strut and then erroneously apply the prescribed increment or decrement in length to a neighboring strut.

Therefore, according to the known solutions, the interaction between the adjusting tool, the struts to be adjusted and the patient is cumbersome and may lead to operation errors. It is thus desirable to provide a system for adjusting external fixation struts that solves, or at least alleviates, the drawbacks identified with respect to the prior art.

It is therefore an aim of the present disclosure to devise a tool for adjusting an external fixation strut having functional and structural features so as to allow to overcome the limits and drawbacks of the prior art solutions, in particular having an improved interaction with the external fixation strut(s), enabling an efficient operation of the same and at the same time the automation/securing of the adjustment process, without burdening to the user with additional tasks such as strut number identification or external measurement of the strut length, and without resorting to wireless data communication between the adjustment tool and the strut, avoiding adjustment errors.

SUMMARY OF THE DISCLOSURE

The solution idea at the basis of the present disclosure is that of providing a programmable tool adapted to couple with one or more struts of an external fixation device and able to exchange operating data with (and also delivering power to) said struts, for example to receive data from a sensor (e.g., a position sensor) of the strut and to use said data by means of an integrated controller that drives automatically said programmable tool for the adjustment of the external fixation strut.

More in particular, the tool of the present disclosure has an innovative interaction with the external fixation struts and is configured to automatically retrieve from a cloud unit the prescription for the patient which the tool is associated with (including the date and/or time of the following adjustment step, and possibly generating an alert) and also obtaining feedback information (such as the actual length of the strut) based on the data communication with the strut, said adjustment being then performed automatically once connected to said struts based on the downloaded prescription and on the feedback information. First of all, the operator (e.g., the surgeon), after having downloaded the prescription data, performs the pairing of the tool with each strut, which is thus univocally associated with said tool (with a univocal strut ID) thanks to the data communication therewith, and thus can be recognized by said tool. The patient is then properly guided in all operating steps, and he/she is only required to press buttons of the tool to confirm and/or start specific operations of said tool and perform the adjustment operation, and, since the association of the struts has been previously performed by the surgeon, an error message is generated if the wrong strut is engaged.

An exemplary tool for adjusting an external fixation strut (the external fixation strut having an adjustment mechanism for length adjustment and a second connecting portion) comprises:

- a first connecting portion adapted to perform data communication with the external fixation strut via the second connecting portion; and
- a controller which includes command instructions and, based on said command instructions, is configured to:
- download prescription data from an external unit, said prescription data relating to a determined patient's case and comprising instructions for performing an adjustment of the external fixation strut of said patient;
- enter a waiting state in which it waits for coupling (i.e., a preliminary coupling) with the external fixation strut of the patient for communicating data therewith via the first connecting portion; the download of the prescription and the preliminary coupling is usually performed by the surgeon (or by any other suitable operator);

after the tool has been coupled with the external fixation strut, recognize a coupling state with the external fixation strut (i.e., recognize the coupling between the tool and the external fixation strut);

based on said coupling (i.e., on said coupling state), communicate with the external fixation strut via the first connecting portion; and once said coupling is complete and data with the external fixation strut have been exchanged, wait for a date and/or time in which the prescribed adjustment is to be applied based on the prescription data.

More in particular, the disclosure comprises the following additional and optional features, taken alone or in combination with each other.

According to an aspect of the present disclosure, during the preliminary coupling, the controller may be configured to assign a strut ID to the external fixation strut.

According to an aspect of the present disclosure, the prescription data may comprise a set of dates and/or times of successive adjustments to be applied to the external fixation strut, as well as it may comprise an extent of the adjustments to be applied.

According to an aspect of the present disclosure, the controller may be configured to generate an alert when the date and/or time of the prescribed adjustment is reached.

According to an aspect of the present disclosure, the state in which the controller waits for the date and/or time when the prescribed adjustment is to be applied may be an idle state.

According to an aspect of the present disclosure, when the date and/or time in which the strut adjustment is to be applied is reached, the controller may be configured to enter a further waiting state in which it waits for a successive coupling (i.e. another coupling following the preliminary coupling) for applying the prescribed adjustment to the external fixation strut, said successive coupling involving a mechanical engagement with said external fixation strut. The successive coupling may be performed by the patient.

According to an aspect of the present disclosure, after being mechanically engaged with the external fixation strut in the successive coupling operation following the further waiting state, the controller may be configured to apply the prescribed adjustment by driving tool means which are adapted to act on the adjustment mechanism of the external fixation strut.

According to an aspect of the present disclosure, during said successive coupling operation, the controller may be configured to retrieve, from the external fixation strut, information relating to said external fixation strut, wherein said information comprise at least a measurement indicative of a length of the external fixation strut, said length being used for feedback control for driving the tool according to the prescription data. Clearly, the length of the strut may be read also during the preliminary coupling by the surgeon.

According to an embodiment, said information may also comprise the strut ID.

According to an aspect of the present disclosure, the controller may be configured to retrieve the measurement indicative of the length of the external fixation strut from a sensor of said external fixation strut, said data passing through the first connecting portion.

According to an aspect of the present disclosure, the controller may be configured to detect from the external unit an update of the prescription data and to download said update in order to substitute the previously downloaded prescription data with updated prescription data.

According to an aspect of the present disclosure, the controller may be configured to postpone the application of the adjustment of the external fixation strut following a selection of the user.

According to an aspect of the present disclosure, in case a postponement is selected by the user, the controller may be configured to apply to the strut, during a next adjustment operation, the adjustment that has been postponed, the adjustment amount that is added during said next adjustment operation being based on an elapsed time from the last performed adjustment operation.

According to an aspect of the present disclosure, the tool may comprise push buttons adapted to be engaged by a user in order to initiate or complete or select operating steps of the tool.

According to an aspect of the present disclosure, the tool may comprise means for communicating data with the external unit.

According to an aspect of the present disclosure, after the coupling (both preliminary and successive) with one external fixation strut is completed, the controller may be configured to check whether other external fixation struts are to be coupled by the tool and, if yes, to enter a waiting state in which it waits for the coupling with said other external fixation strut.

According to an aspect of the present disclosure, the controller may be configured to generate an alert in case the patient couples (engages) the tool with a wrong strut.

According to an aspect of the present disclosure, the controller may be configured to generate interfaces on a display of the tool, these interfaces being structured to show a respective operating status of the tool.

According to an aspect of the present disclosure, the tool may comprise an output shaft, and a motor operable to rotate said output shaft, wherein the controller is configured to drive the motor according to the prescription data.

According to an aspect of the present disclosure, the controller may be configured to monitor the rotation of the output shaft and to evaluate gearbox reduction rates between the motor of the tool and the strut.

According to an aspect of the present disclosure, the tool may further comprise a first coupling portion solidly attached to the output shaft and adapted to releasably engage with a corresponding second coupling portion of the adjustment mechanism of the strut, thereby enabling torque transmission from the motor to the adjustment mechanism, wherein the first connecting portion is in electrical communication with the controller and is adapted to electrically connect with the second connecting portion when the first coupling portion is engaged with the second coupling portion, thereby enabling data transmission from the external fixation strut to the controller, and vice versa.

According to an aspect of the present disclosure, the tool may further comprise a power supply, and the electrical connection between the first connecting portion and the second connecting portion further enables power transmission to the external fixation strut.

The present disclosure also relates to an external fixation strut comprising an elongated body comprising at least a first shaft and a second shaft moveable with respect to each other to modify the length of said elongated body, an adjustment mechanism for moving the second shaft with respect to the first shaft thereby modifying the length of the elongated body, a second coupling portion of the adjustment mechanism adapted to releasably engage with a first coupling portion of a tool as disclosed above (according to any one of the above features, alone or in combination) to enable torque transmission, at least a sensor adapted to perform at least a measurement which is indicative of the length of the elongated body, and a second connecting portion of the adjustment mechanism which is in electrical communication with a first connecting portion of the programmable tool when the first coupling portion is engaged with the second coupling portion, and which enables transmission of data from the sensor to the tool.

According to an aspect of the present disclosure, the sensor may be a position sensor.

According to an aspect of the present disclosure, the second connecting portion may also be adapted to receive power signals from the tool.

The present disclosure also relates to a medical assembly a tool as disclosed above and one or more external fixation struts as disclosed above.

The features and advantages of the tool of the present disclosure will result from the description, made hereinafter, of one or more embodiments thereof with reference to the attached drawings.

BRIEF DESCRIPTION OF THE DRAWINGS

For a more complete understanding of the features and advantages of the present disclosure, reference is now made to the detailed description of the disclosure along with the accompanying figures and in which:

FIG. 7 is a side view of a second embodiment of an external fixation strut according to the present disclosure;

FIG. 8 is a cross-sectional view of an external fixation strut, taken along the cutting plane referenced with D-D in FIG. 7;

FIG. 9 is a cross-sectional view of an external fixation strut, taken along the cutting plane referenced with E-E in FIG. 7;

DETAILED DESCRIPTION

While the making and using of various embodiments of the present disclosure are discussed in detail below, it should be appreciated that the present disclosure provides many applicable inventive concepts that can be embodied in a wide variety of specific contexts. The specific embodiments discussed herein are merely illustrative of specific ways to make and use the disclosure and do not limit the scope of the disclosure.

With reference to the above figures, a tool for adjusting an external fixation strut according to the present disclosure is globally and schematically indicated with 100, while an external fixation strut is globally and schematically indicated with 200.

It is worth noting that the figures represent schematic views and are not drawn to scale, but instead they are drawn so as to emphasize the important features of the disclosure. Moreover, in the figures, the different elements are depicted in a schematic manner, their shape varying depending on the application desired. It is also noted that, in the figures, the same reference numbers refer to elements that are identical in shape or function. Finally, particular features described in relation to an embodiment illustrated in a figure are also applicable to the other embodiments illustrated in the other figures.

Clearly, some technical details of the disclosure can be replaced by other technically equivalent details without departing from the claimed protection scope, as the skilled man well knows.

Moreover, when sequences of process steps are illustrated, they do not necessarily follow the indicated sequence, said steps can be inverted unless it is not expressly indicated otherwise.

The programmable tool 100 of the present disclosure is adapted to adjust the external fixation strut 200 by implementing an enhanced interaction therewith and by communicating with an external unit, such as a cloud unit and/or a user device, as it will disclosed in the following.

Figures 1, 2, 3:
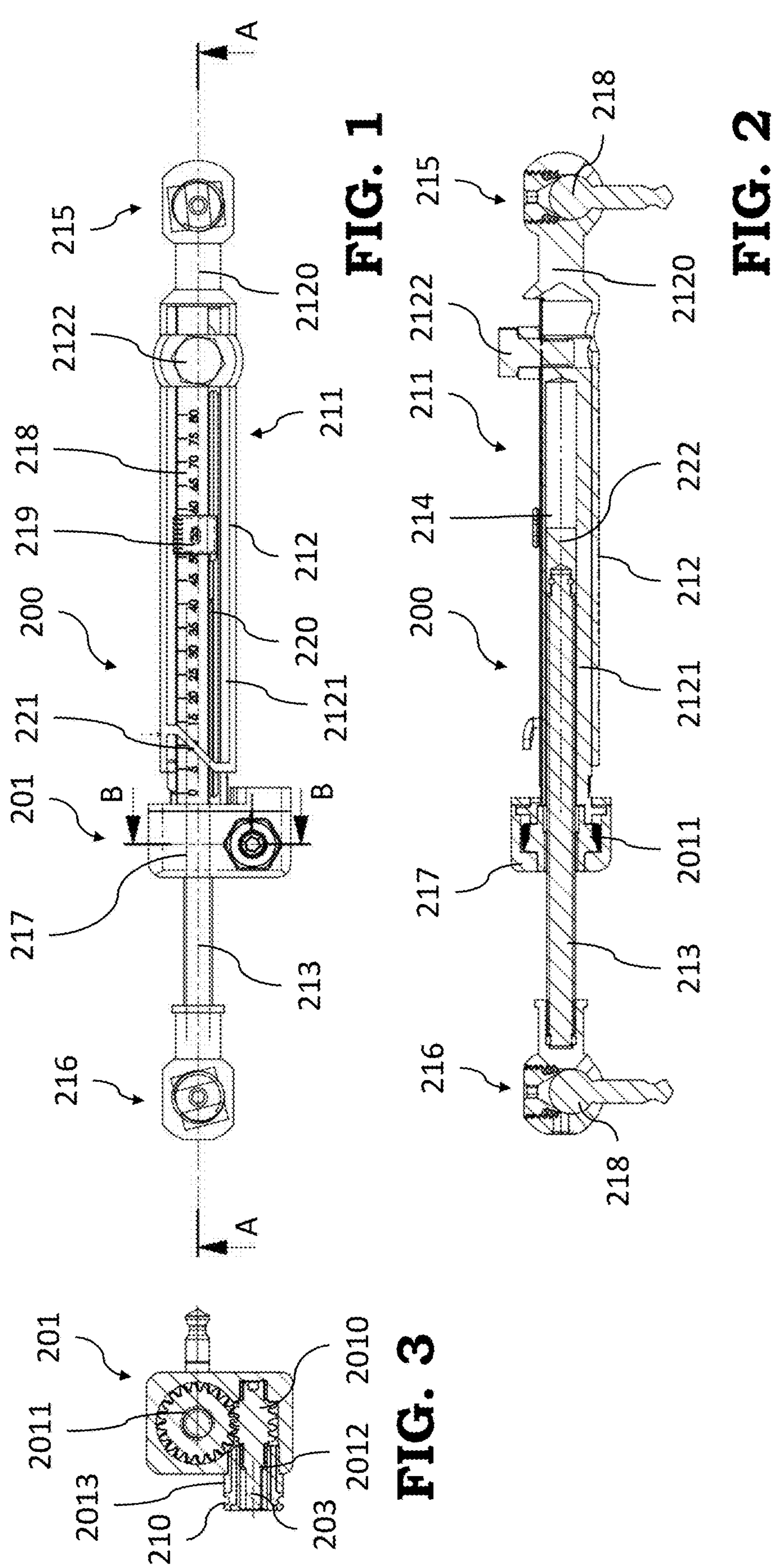
FIG. 1 is a side view of an embodiment of an external fixation strut according to the present disclosure.
FIG. 2 is a cross-sectional view of an external fixation strut, taken along the cutting plane referenced with A-A in FIG. 1.
FIG. 3 is a cross-sectional view of an external fixation strut, taken along the cutting plane referenced with B-B in FIG. 1.

FIG. 1 shows a schematic side view of an external fixation strut 200 according to the present disclosure comprising an elongated body 211 with opposite ends 215, 216 configured to be attached to a respective fixation ring or arch of an external fixator, preferably of the hexapod type.

The rings of the external fixator, which can be fixed to bone sites via half pins or wires, are known per se and not depicted in the enclosed figures.

The elongated body 211 is formed by a first hollow tubular shaft 212 in which a second tubular shaft 213 is slidably hosted. The first shaft 212 is in turn composed of a hollow main body 2120, which culminates with the first end 215, and a slidable body 2121 which slides within the main body 2120 and houses the second tubular shaft 213.

The relationship between the two bodies of the first 212 shaft and between the first shaft and the second shaft 213 confers a telescopic configuration to the ensemble of the strut 200, so that the elongated body 201 may be adjusted in its length according to the needs of keeping the interconnected rings in a predetermined relative spatial relationship.

In particular, the relationship between the main body 2120 and the sliding body 2121, which defines the length of the first shaft 212, is varied in a first regulation of the length between the two attachment points of the strut 200, while the relationship between the first shaft 212 and the second shaft 213 is varied to finely adjust the strut length, in particular in a postoperative follow-up.

The main body 2120 and the sliding body 2121 are locked together by a locking screw 2122, which is released for manual adjustment of the relative position of the two elements.

On the contrary, the position of the second shaft 213 with respect to the first shaft 212 is adjusted through a rotatable adjustment mechanism 201 contained in a casing 217 of the sliding body 2120 of the first shaft 212. The rotatable adjustment mechanism will be described in greater detail with reference to FIG. 3.

An external metering cursor 219, which is solidly attached to an inner end of the second shaft 213 through a leg traversing a longitudinal slit 220 of the casing 217, slides along a graduated scale 218 integral with the casing 217 and makes it possible to visually assess the relative position of the second shaft 213 with respect to the first 212.

To make the graduated scale 218 visible to the user, the frame of the hollow main body 2120 has an open side. A transverse bridge 221 of the frame is provided at an end of said open side. The bridge 221 is visible against the background of the graduated scale 218, making it possible to visually assess the relative position of the sliding body 2121 with respect to the main body 2120, i.e. the length of the first shaft 212.

FIG. 2 shows a cross-sectional view of the device of FIG. 1.

At the two ends 215, 216 of the strut 200, ball-joints 218 are provided which makes it possible to articulate the strut 200 with respect to a fixation ring or arch to which it is attached.

The rotation imparted through the rotatable adjustment mechanism 201 defines, through a threaded connection, a sliding of the second shaft 213 with respect to the first shaft 212, so that the second end 216 or dragged towards the first end 215.

FIG. 3 shows a cross-sectional view of the above-mentioned rotatable adjustment mechanism 201.

The rotatable adjustment mechanism 201 comprises a worm gear mechanism having a worm screw 2010 meshing with a worm gear 2011, the latter being coaxial with the second shaft and threadingly engaged with it.

The worm screw 2010 has a worm screw shaft 2010 which is orthogonal to the axis of the elongated body 211. A protruding head 2013, which protrudes from a lateral wall of the casing 207, rotatingly houses said screw shaft 2010 and, as will be further discussed in the following, defines a second coupling portion 203 for the attachment of a corresponding coupling portion of a wrench tool.

The protruding head 2013 further defines an outer sleeve surrounding the second coupling portion 203. In the depicted embodiment, the outer sleeve has an inner circular profile and an outer hexagonal profile, the latter comprising an external groove 210 for attachment of a locking mechanism of an adjustment tool.

Figures 4, 5:
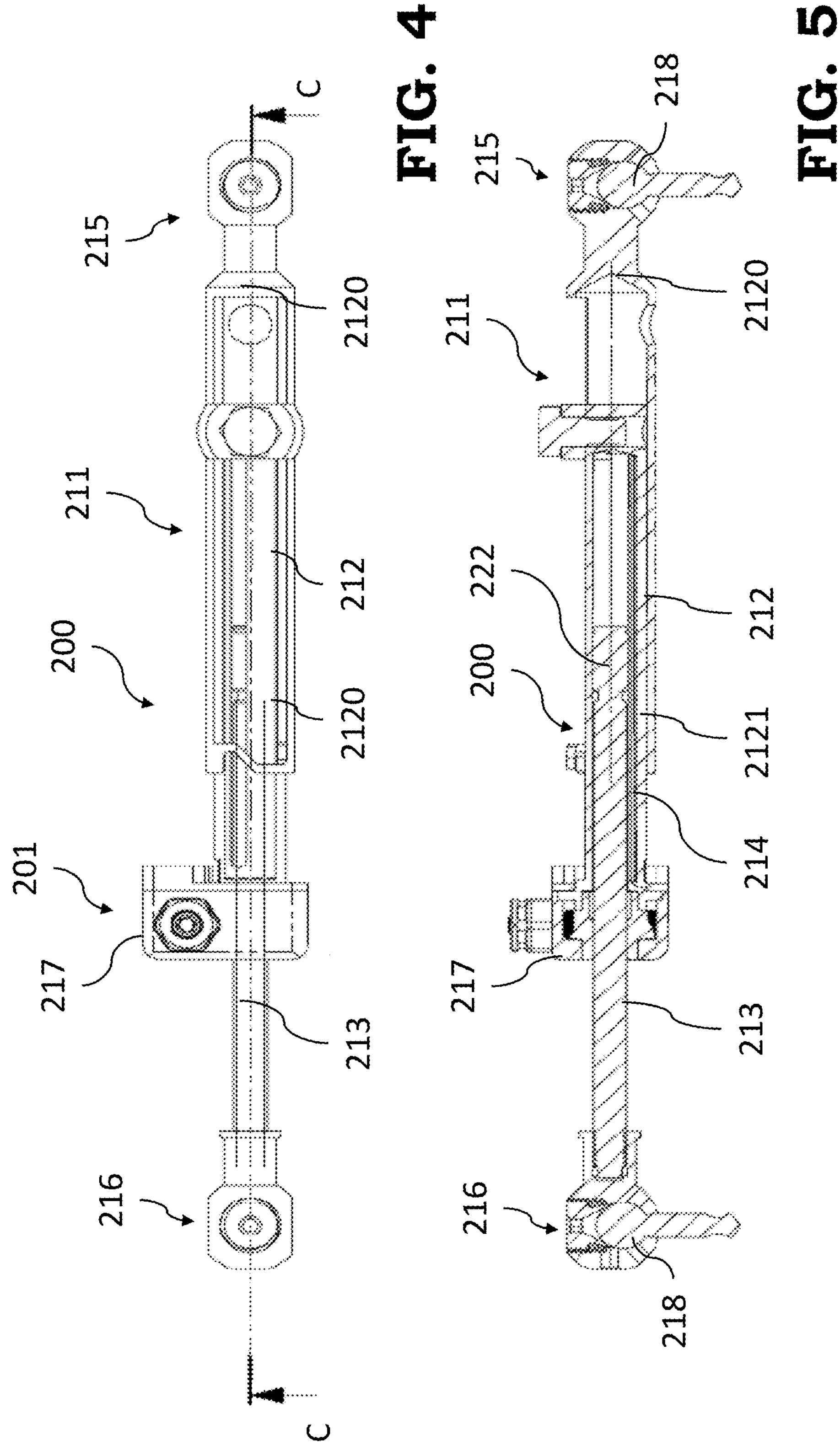
FIG. 4 is a side view of an embodiment of an external fixation strut according to the present disclosure.
FIG. 5 is a cross-sectional view of an external fixation strut, taken along the cutting plane referenced with C-C in FIG. 4.

FIG. 4 shows a schematic side view of the external fixation strut 200 according to the disclosure, with no further elements disclosed.

FIG. 5 shows a cross-sectional view of the device of FIG. 4.

A position sensor 214 is housed within the casing 217, solidly attached to it and it extends along the longitudinal inner length of the first shaft 212.

The position sensor 214 detects an absolute position of an end-piece 222 of the second shaft 213 and/or of the external metering cursor 219, returning a measurement value which can be employed to assess the relative position of the second shaft 213 with respect to the first shaft 212.

Said measurement value may then be used as a feedback information when adjusting the length of the external fixation strut 200 during the postoperative phase, as it will be disclosed into details in the following.

Preferably, the position sensor 214 is a capacitive sensor but other alternatives, such as an inductive solution, can be employed. In both instances, an absolute sensor is preferred over a relative sensor.

Figure 6:
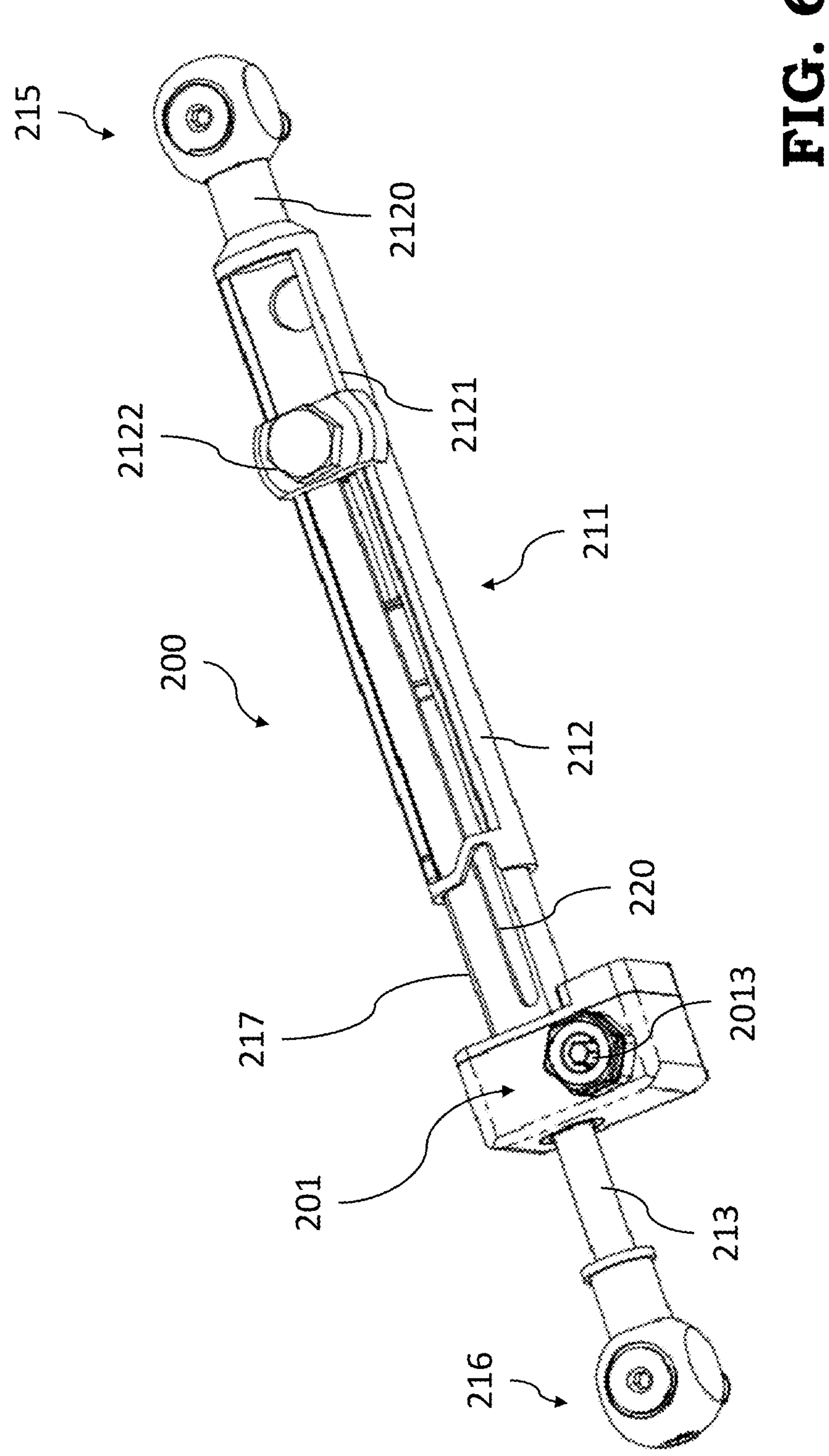
FIG. 6 is a perspective view of an embodiment of an external fixation strut according to the present disclosure.
Figures 10, 11, 12:
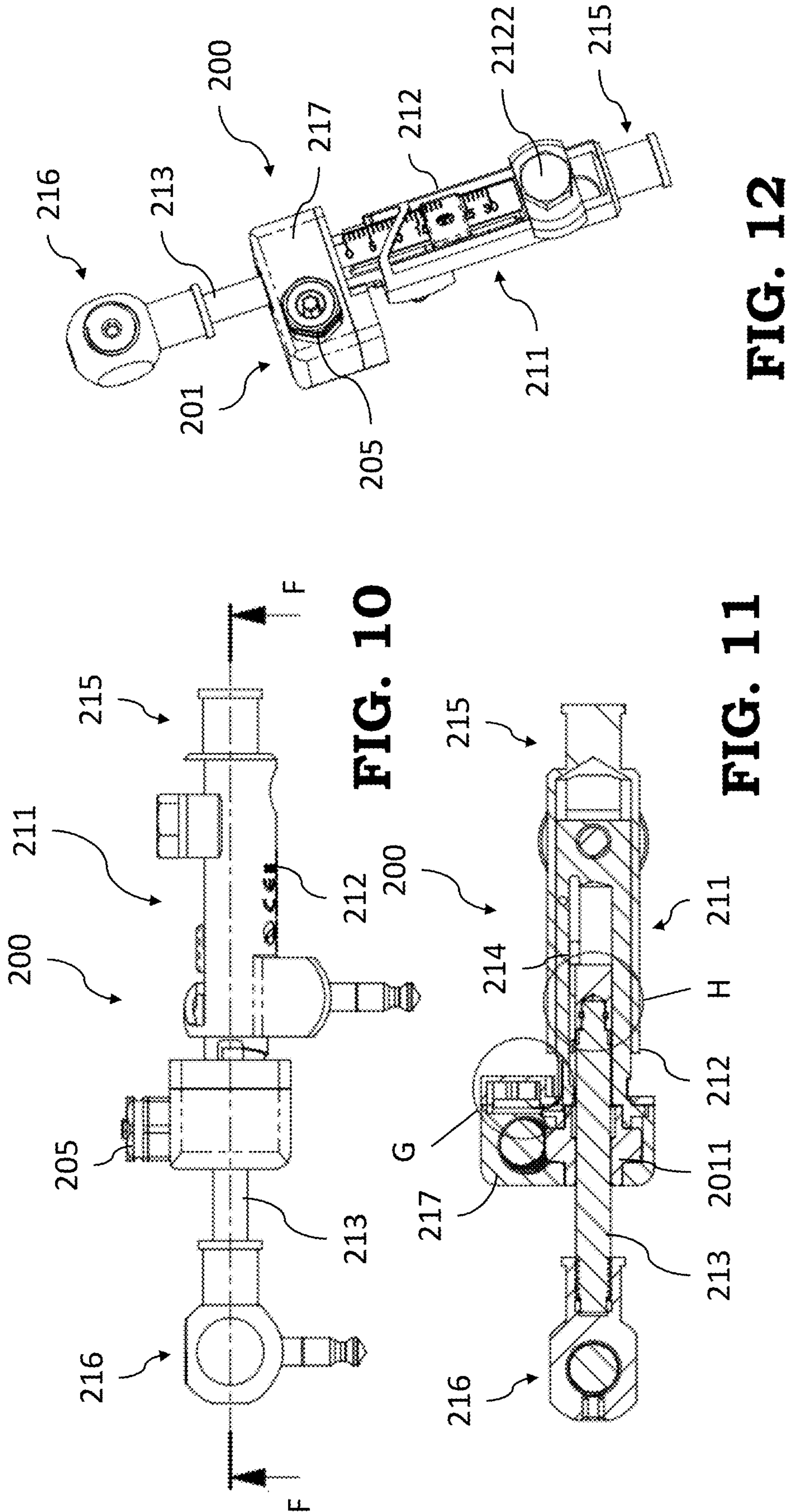
FIG. 10 is a side view of a second embodiment of an external fixation strut according to the present disclosure.
FIG. 11 is a cross-sectional view of an external fixation strut, taken along the cutting plane referenced with F-F in FIG. 10.
FIG. 12 is a perspective view of a second embodiment of an external fixation strut according to the present disclosure.

FIG. 6 shows a schematic perspective view of the external fixation strut 200 according to the disclosure, with no further elements disclosed.

FIGS. 7-12 refer to an alternative embodiment of the external fixation strut, which is shorter in size with respect to the long external fixation struts previously discussed.

In such an alternative embodiment, the external fixation strut essentially has the same components and main features of the longer embodiments, which are previously described. Such components and features are therefore indicated in the figures by reference numerals previously used, and they are not described anew in the following paragraphs.

The main structural difference with respect to the longer version is that here the two attachment points defined by the ball-joints 218 are set closer to each other, thanks to the fact that the ball-joint of the first shaft 212 is not placed at the end 215 thereof, but rather at an opposite end of the hollow main body 2120 of the first shaft 215.

Figure 14:
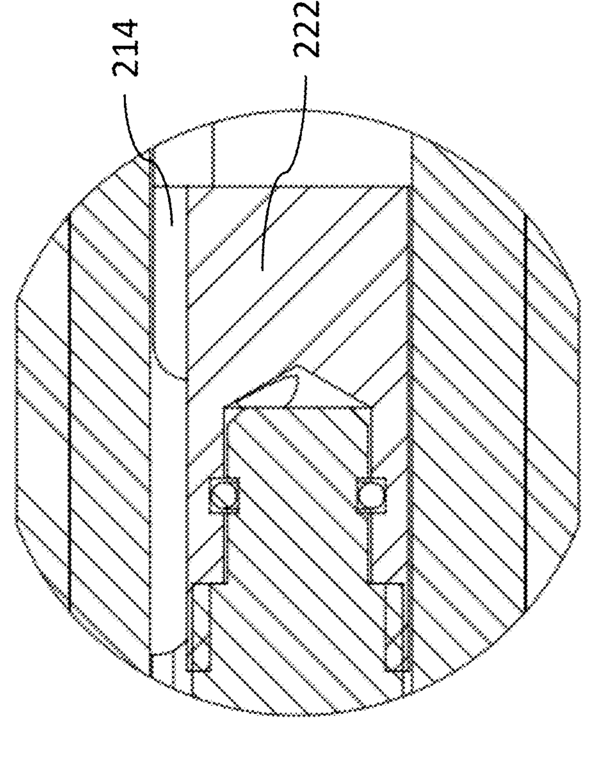
FIG. 14 is an enlarged detail of the area referenced with H in FIG. 11.
Figure 13:
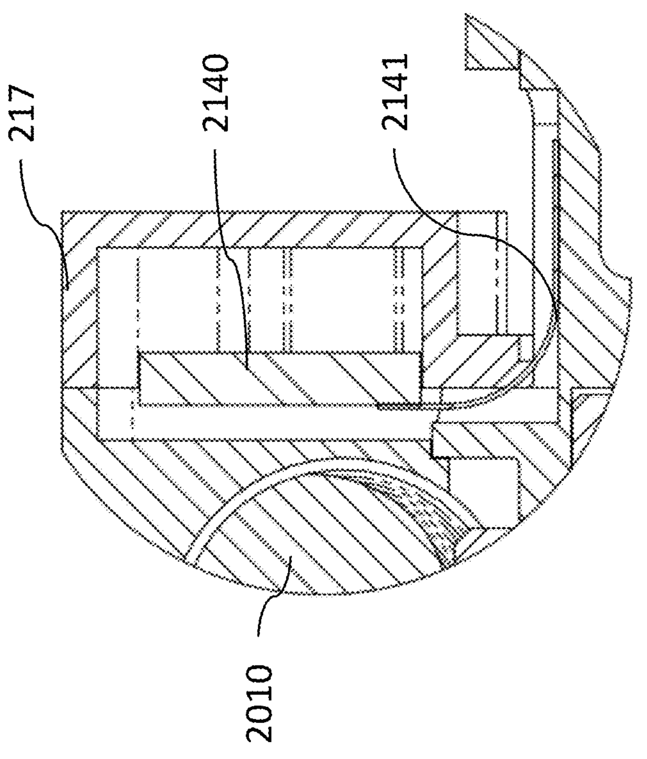
FIG. 13 is an enlarged detail of the area referenced with G in FIG. 11.

FIGS. 13 and 14 show peculiar details in the construction of the previously introduced position sensor 214.

A flexible signal line 2141 of the position sensor connects an input pad 2140 or board to the body of the sensor 214, which extends in the vicinity of the sensed end-piece 222.

It is observed that the flexible signal line 2141 has at least one curvature to connect the rotatable adjustment mechanism's housing to the rest of the shaft. Said curvature is designed such that the radius is kept above a threshold value to avoid damaging the signal line during the manufacturing process.

In order to adjust the external fixation strut, the programmable tool 100 is used, as it will be disclosed into details in the following, with reference to FIG. 15 and following.

Figure 15:
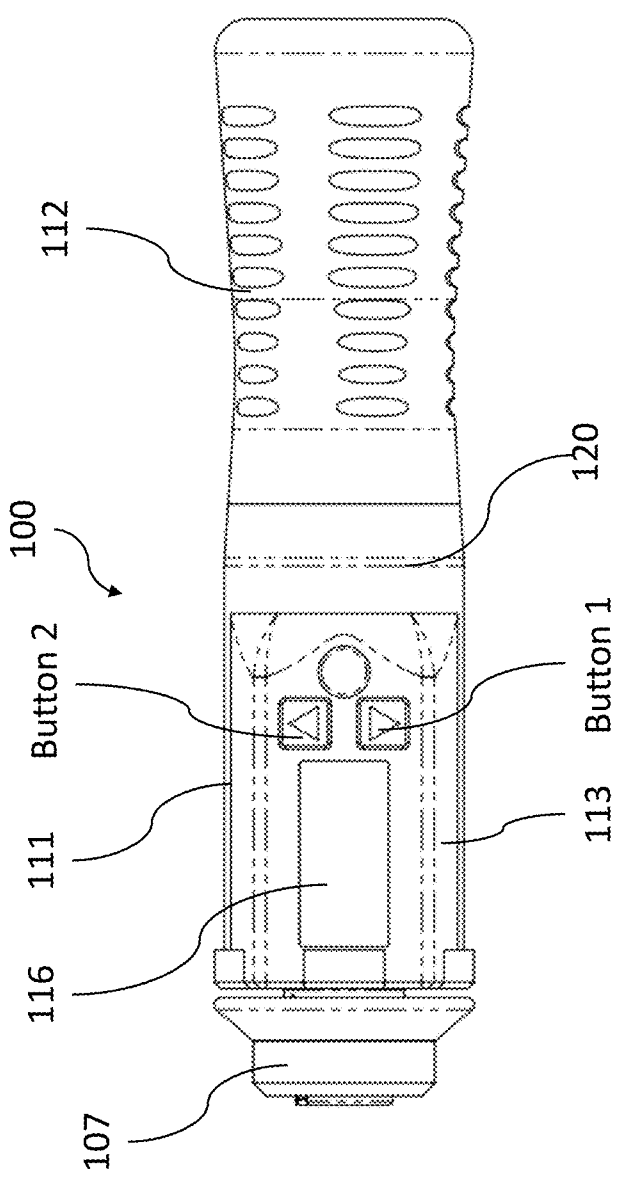
FIG. 15 is a top view of an embodiment of a programmable tool according to the present disclosure.

FIG. 15 shows a top view of the programmable tool 100 according to the present disclosure, which is in the form of a wrench, in particular an electronic wrench.

The wrench comprises a rigid external casing 111.

In the depicted embodiment, the casing 111 has a substantially cylindrical shape. However, the shape of the casing 111 may be any shape and size convenient for use.

In the depicted embodiment, the casing 111 defines a handpiece having a distal gripping portion 112 with an ergonomic handle followed by a proximal interface portion 113.

The casing 111 may have a variety of connection ports, connectors, display and controls.

In particular, in the depicted exemplary embodiment, the interface portion comprises a first pushbutton and a second pushbutton 114 and 115, herein identified also as Button 1 and Button 2, a display 116, and further has an indicator 120, such as an annular LED indicator (e.g., including a RGB LED), which can be lit in various colors and in a steady or pulsing mode in order to signal a plurality of device operational statuses to the user.

In a preferred embodiment, the annular LED indicator may have up to four lighted states, respectively signaling: a call to action by the user, an ongoing operation by the wrench, successful or unsuccessful completion of a wrench operation. In an embodiment, there may be a further state of the LED indicator, said further state indicating for example a charging operation.

The device may further comprise a buzzer or any other audio device. Moreover, the device may also comprise wireless charging means, as well as Near-Field Communication (NFC) means for communication with other electronic devices, as it will be detailed below.

The device further comprises a front muzzle 107 ahead of the interface portion 113, which is arranged to connect to the torque input port of the rotatable adjustment mechanism 201 of the external fixation struts 200.

Figures 16, 17:
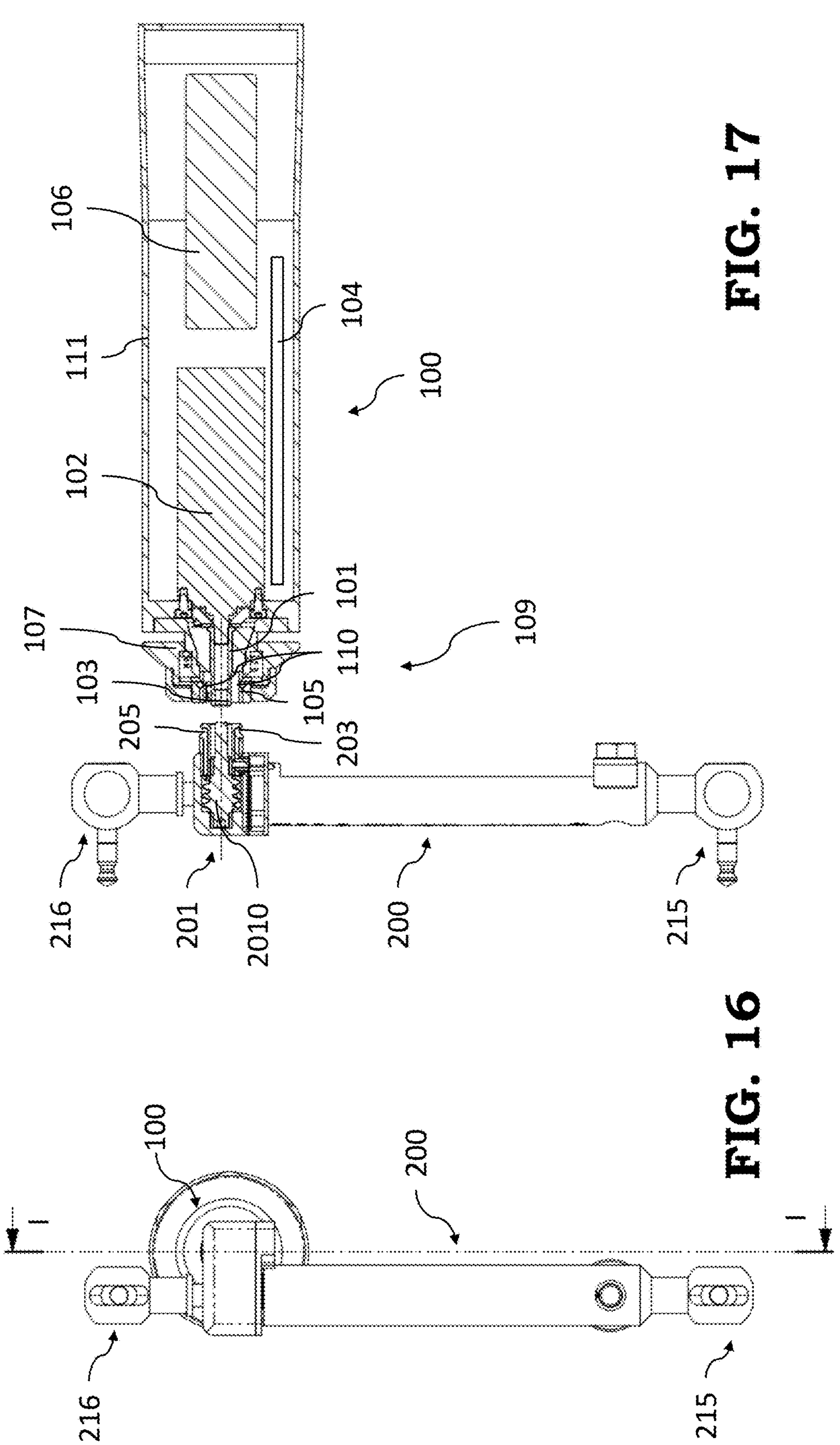
FIG. 16 is a side view of an embodiment of an external fixation strut next to an embodiment of a programmable tool, according to the present disclosure.
FIG. 17 is a cross-sectional view of an external fixation strut next to a programmable tool, taken along the cutting plane referenced with I-I in FIG. 16.

FIG. 16 shows a side view of the programmable tool 100 about to be coupled with an external fixation strut 200.

FIG. 17 is a cross-sectional view of the two devices of FIG. 16, and schematically shows the main components inside the casing 111 of the programmable tool 100.

The programmable tool 100 comprises a power source 106 in the form of a rechargeable battery, an electric motor 102 which preferably comprises a gearbox in-line with a coaxial output shaft 101, and a controller 104, for example in the form of a PCB. The controller 104 is adapted to manage the operation of the tool 100 and is not limited by a particular configuration.

The programmable tool 100 may also comprise an internal memory, which can be conveniently used for storing a patient's prescription and an actual length of a plurality of struts making up an external fixator to be adjusted by the tool 100. In any case, the present disclosure is not limited by the architecture of the tool memory, which may be an integral part of the controller 104 or also a separate memory portion which is operatively connected to said controller 104.

The programmable tool 100 further comprises means (herein referred to as "TX") for communicating data with an external unit, in particular with an external data source, for example in the form of data ports and/or wireless connectivity. Preferably, the programmable tool has a SIM housing (not shown) which is meant to provide internet connectivity to the device, even if any other suitable means may be used for this purpose. Such means TX may also comprise Bluetooth connection ports or Wi-Fi connection ports, as well as the above-mentioned NFC means, for example for connecting with a user device or other external devices.

In some embodiments, means for a wireless charge can be provided.

The controller 104 of the programmable tool 100 is adapted to communicate with the external unit, in particular with a cloud unit, directly or via a portable electronic user device such as a smartphone, to retrieve a surgeon's prescription and update a status comprising at least the length of the several external fixation struts 200 of an external fixator, as it will be disclosed in the following with reference to figures from 21 to 25.

The controller 104 is connected to the pushbuttons 114, 115, display 116 and annular LED indicator in order to read user's commands, communicate status updates, or guide the user throughout a process of adjusting all of the struts 200 according to a given prescription.

The muzzle 107 of the programmable tool 100 houses the output shaft 101, which culminates with a first coupling portion 103 in the form of a wrench socket, in particular a hex socket.

The muzzle further comprises a locking mechanism 109 operable to secure and selectively release the engagement of the first coupling portion 103 with the second coupling portion 203. When the locking mechanism 109 is engaged the protruding head 2013 of the rotatable adjustment mechanism 201 is housed within an annular recess 108 of the muzzle 107, best shown in FIG. 20.

Figures 18, 19, 20:
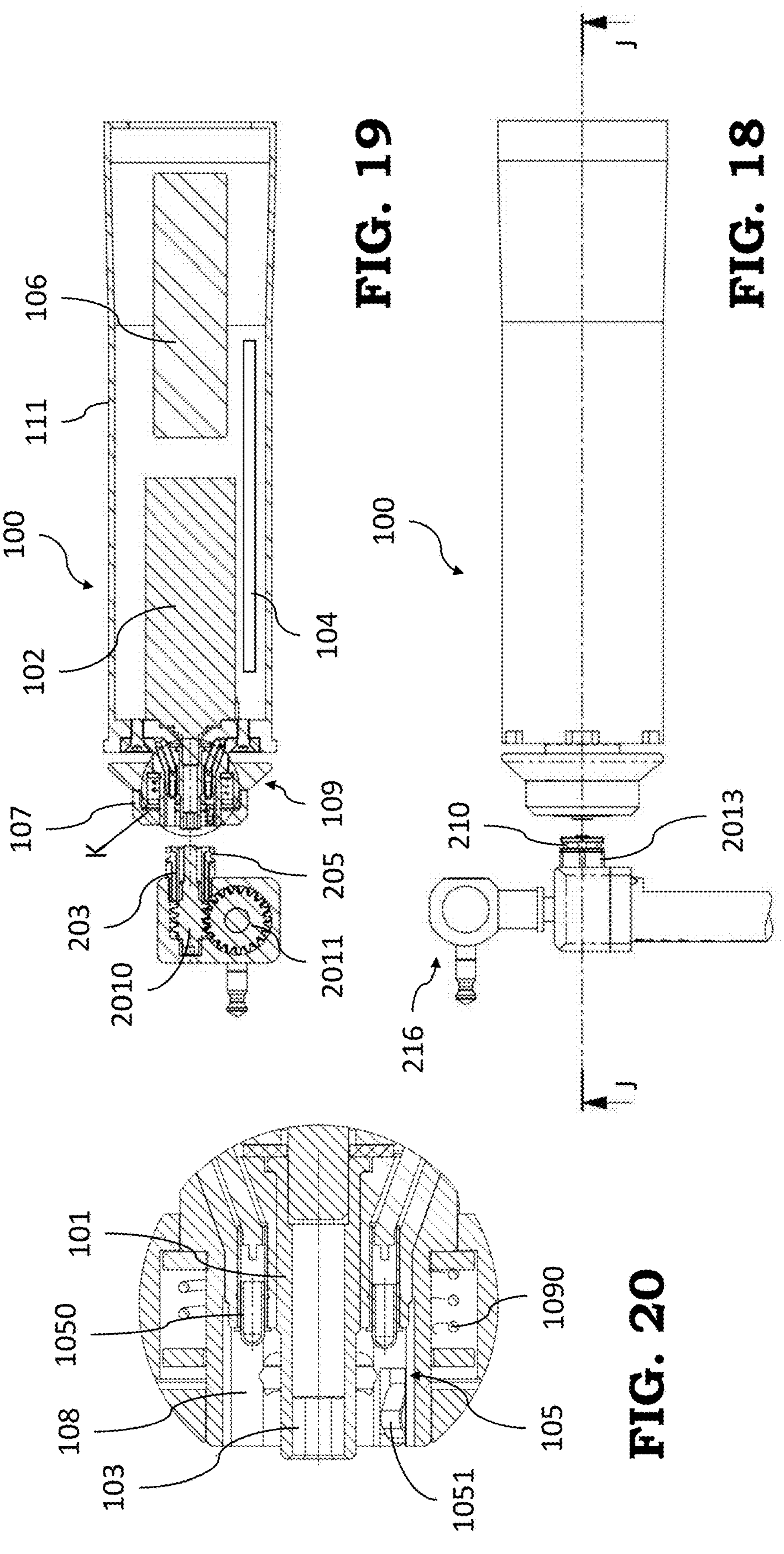
FIG. 18 is a side view of an embodiment of an external fixation strut next to an embodiment of a programmable tool, according to the present disclosure.
FIG. 19 is a cross-sectional view of an external fixation strut next to a programmable tool, taken along the cutting plane referenced with J-J in FIG. 18.
FIG. 20 is an enlarged detail of the area referenced with K in FIG. 19.

The locking mechanism 109 is defined by the body of the muzzle 107, which may be retracted towards the programmable tool 100 housing 111 pressing it against elastic means, which may be in the form of a spring 1090 best shown in FIG. 20. The muzzle 107 internally has latching elements 110, which may be in the form of rollers moving along oblique paths, said roller being externally biased by the action of the spring 1090 in order to engage.

Furthermore, the tool 100 comprises a first connecting portion 105 (for example arranged around the first coupling portion 103), which is meant to electrically connect with a second connecting portion 205 of the strut 200.

When the locking mechanism 109 is engaged, the first connecting portion 105 is connected to the second connecting portion 205 of the strut 200 and data connection is provided which allows the controller 104 to retrieve data from sensor 214.

The electric connection further ensures powering of the sensor 214 from the power source 106.

FIG. 18 shows a further side view of the programmable tool 100 about to be coupled with an external fixation strut 200.

FIG. 19 is a cross-sectional view of the two devices of FIG. 18.

FIG. 20 is an enlargement of FIG. 19, which shows a detail of the first connecting portion 105, according to an exemplary embodiment of the present disclosure.

The first connecting portion 105 comprises a plurality of inner connector 1050 at the bottom of the annular recess 108, which are preferably in the form of pogo-pins, meant to connect a first electric pole.

Further, the first connecting portion 105 comprises a plurality of outer connectors 1051, preferably in the form of clip or leaf spring connectors, projecting from the outer lateral surface of said annular recess 108. Said outer connectors 1051 are meant to connect a second electric pole.

In use, the inner connectors 1050 contact an inner surface 2050 of the protruding head 2013 outer sleeve, while the outer connectors 1051 contact an outer surface 2051 of the same sleeve. As best seen in FIG. 9, said inner surface 2050 and outer surface 2051 are separated by a dielectric layer 2052.

In order to improve the interaction of the tool 100 with the external fixation strut 200, advantageously according to the present disclosure, the controller 104 comprises a set of instructions that, when executed, cause the tool 100 to automatically perform the operations disclosed below.

Figure 21:
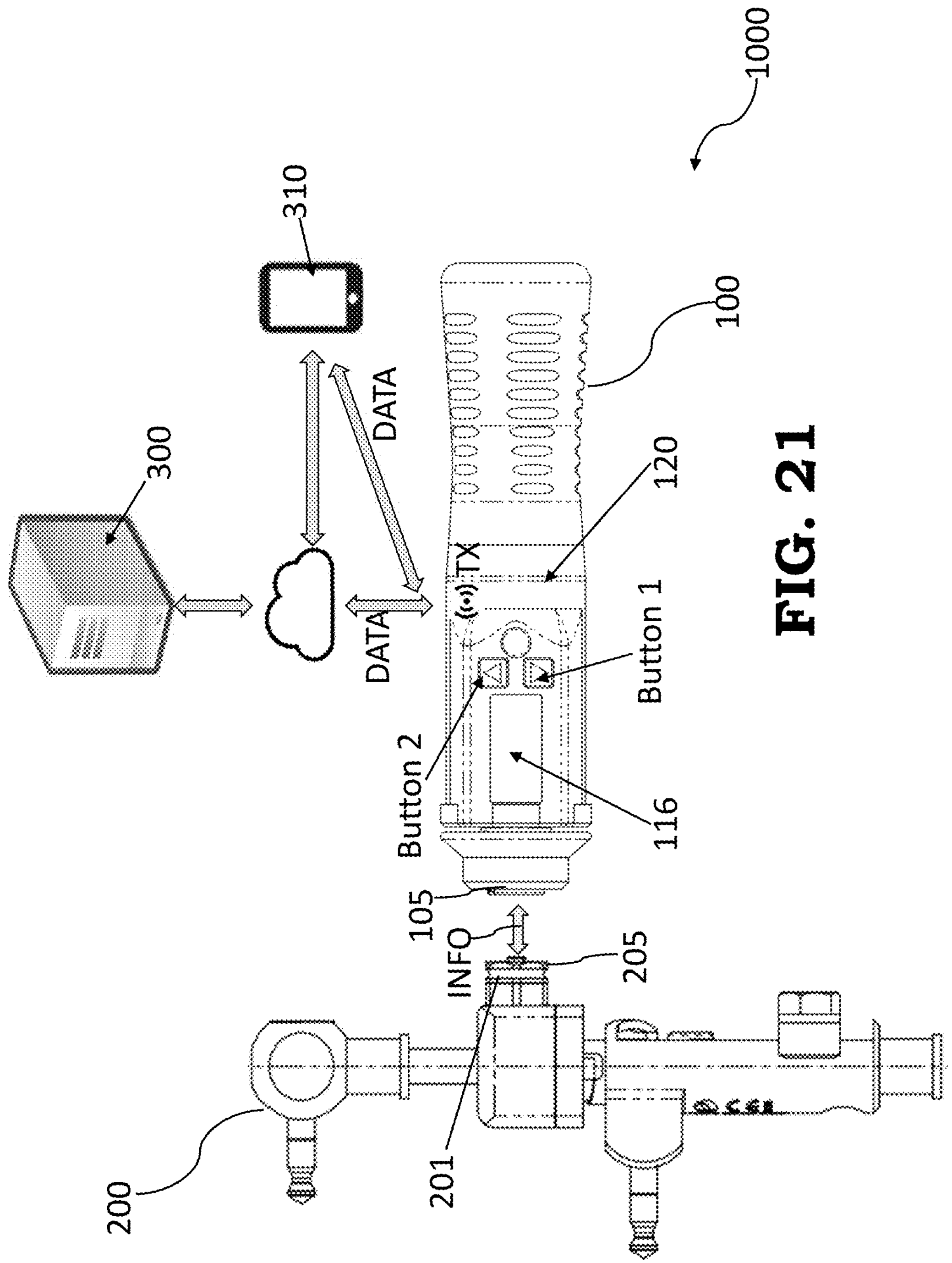
FIG. 21 is a general scheme of a medical assembly according to the present disclosure, wherein a tool interacts with an external unit and with the external fixation strut.

FIG. 21 is a general scheme of a medical assembly 1000 including the tool 100 and the external fixation strut 200 having the above-disclosed rotatable adjustment mechanism 201 for length adjustment. As seen before, the external fixation strut 200 comprises the second connecting portion 205 for data communication with the tool 100. On the other hand, the tool 100 comprises the first connecting portion 105 which is adapted to perform data communication with the external fixation strut 200 via the second connecting portion 205.

Therefore, as mentioned before, the first connecting portion 105 and the second connecting portion 205 also enable data transmission between the external fixation strut 200 and the controller 104 of the tool 100, for example from the sensor of the external fixation strut 200 to the controller 104.

In operation, the controller 104 is first of all configured to allow the tool 100 to be associated with a specific patient's case. For example, the controller 104 may allow loading in the memory of the tool 100 the information relating to the patient and recalling said information when needed (for example upon turning on the tool 100 when this association phase is started). The surgeon (or any other suitable operator) may then confirm the performed association and go to the next operating step, for example by pressing one of the push buttons of the tool 100 (e.g., button 1). This first association is thus performed and confirmed by the surgeon, setting up the tool for the following patient's use.

Suitably, once associated with the specific patient, the controller 104 is configured to download the prescription data (herein referred to as "DATA") related to said patient from the above-mentioned external unit (herein identified by the reference number 300), such as a cloud unit. In some embodiments, the download may occur automatically.

The external unit 300 may be for example a web server to which the tool 100 accesses either directly or indirectly, through the means TX thereof.

For example, the tool 100 may be connected, via the means TX, to a user device 310 such as a smartphone, which is equipped with a suitable application or is able to access a dedicated internet portal to perform the connection with the external unit 300 and download into the tool 100, in particular into the memory thereof, the prescription data DATA.

Therefore, the download of the data may occur directly via the tool 100 itself, or indirectly via a user device, this applies also to subsequent updates to be downloaded.

The prescription data DATA relate to the patient's case which the tool 100 is associated with and comprise the information and instructions for performing an adjustment of the external fixation strut 200 of said patient, such as for example a set of dates and/or times in which the adjustment of said external fixation strut 200 is to be applied, as well as the extent of said adjustment, for example in terms of strut length per adjustment step.

It is observed that each prescription has an expiry date. If no prescription is downloaded within that date, the prescription become invalid, and no other treatment is allowed Once the download is complete, the surgeon (or any other suitable operator) may confirm by pressing one of the push buttons of the tool 100 (e.g., button 1). Therefore, in standard setup operations, the surgeon confirms the successful download of the prescription data DATA, as above discussed. As it will be discussed below, in case of a prescription update, the patient may receive said update (for example via a mobile app) and then he/she may confirm the download of the updated prescription and may then confirm its success.

Once the above preliminary operations (i.e., preliminary association and prescription download) are completed by the surgeon (or by any other suitable operator), the controller 104 then causes the tool 100 to enter a waiting state, for example following a further pressure of one of the push buttons, in which it waits for a preliminary coupling with the external fixation strut 200 of the patient, in particular for communicating data therewith via the first connecting portion 105.

Also in this case, this preliminary coupling is performed by the surgeon (or by any other suitable operator); in particular, after the tool 100 has been connected to the external fixation strut 200 in the preliminary coupling operation, the controller 104 is able to automatically recognize a coupling state of the tool 100 with said external fixation strut 200 and to signal this coupling state.

Then, based on this coupling, the controller 104 communicates with the external fixation strut 200 via the first connecting portion 105 and the second connecting portion 205, in particular it performs a data communication.

In particular, in this preliminary coupling, the controller 104 is able to write an ID to the strut memory in order to give a unique identity to a brand new strut, or to re-code a wrong-coded strut. In other words, during said preliminary coupling, the controller 104 is configured to assign a strut ID to the external fixation strut 200 for the identification thereof.

In this coupling, it is also possible to exchange other preliminary information with the struts (e.g., if an ID has already been assigned, to read said ID, as well as reading the length of the strut, as it will be detailed in the following).

Then, after having been coupled with the external fixation strut 200 and having exchanged preliminary information therewith (i.e., after the above preliminary coupling), the tool 100 (i.e., the controller 104 thereof) enters an idle state (for example following a further pressure of a push button after the coupling is complete) in which it waits for the prescribed time/date when the strut adjustment is to be applied.

In this idle state, the patient may also check the next adjustment date/time, for example by pressing a push button of the tool 100.

When the date and/or time of the strut adjustment is reached, the tool 100 may generate an alert (which may be a visual and/or acoustic alert) and the patient may press a push button (for example button 1) of said tool 100; the controller 104 is then configured to cause the tool 100 to enter a further waiting state in which it waits for a successive mechanical coupling with the external fixation strut 200 for applying the prescribed adjustment thereto. This successive coupling operation involves a mechanical engagement between the tool 100 and the tool 200 and it is usually performed by the patient.

The controller 104 is configured to wake-up the tool 100 due to an upcoming treatment. In an embodiment, the wake-up of the tool 100 is performed by using internal RTC.

In an embodiment, when there is an upcoming treatment, the controller 104 is also programmed to estimate the power-budget to finish the entire treatment.

Then, when the tool 100 is mechanically engaged with the external fixation strut 200 by the patient, the controller 104 is configured to automatically apply the prescribed adjustment by driving dedicated means of the tool 100 which act on the rotatable adjustment mechanism 201 of the external fixation strut 200. More in particular, the controller 104 is configured to drive the motor 102 of the tool 100 according to the prescription data DATA, so as to apply the proper adjustment to the strut 200. As it will be discussed in the following, the length of the external fixation strut 200 may be used for controlling the driving means of the tool 100.

When the tool 100 is engaged with the external fixation strut for correction, the patient is informed when the tool has successfully adjusted the strut gradual length and, by newly pressing a push button (e.g., button 1), the tool may return again in the idle state.

Usually, a fixation device comprises a plurality of struts, for example six struts. Therefore, after the coupling with one external fixation strut is completed, the controller 104 is configured to check whether other external fixation struts are to be engaged by the tool 100 and, if yes, to cause said tool 100 to enter a waiting state (for example after pressing a push button) in which it waits for the coupling with said another external fixation strut. This applies both to the preliminary coupling performed by the surgeon both to the mechanical engagement performed by the patient, wherein said patient is precisely guided and errors are avoided due to previous paring and the generation of errors messages.

Therefore, in an embodiment, after the surgeon has performed the preliminary pairing between the tool 100 and the struts 200, the tool 100 knows exactly the identity of each strut 200 of the external fixation device (e.g., which is the correct strut 1, strut 2, etc.). In this way, if the patient engages the wrong strut, the tool 100 is adapted to returning this feedback to the user and therefore generates a warning in the form of an error message, so that the patient knows that he/she's engaging the wrong strut.

When the patient engages the strut 200 with the tool 100, the latter retrieves useful information (herein referred to as "INFO") from said external fixation strut 200, such as the length thereof.

In an embodiment, the actual length of the external fixation strut 200 is obtained by the controller 104 by reading data from the position sensor 214 of said external fixation strut 200.

Therefore, the information INFO (exchanged during the successive coupling performed by the patient) may relate to a measurement indicative of a length of the external fixation strut 200, and, when the tool 100 is coupled with the external fixation strut 200, the controller 104 is configured to retrieve from the position sensor 2014 of said external fixation strut 200 at least said length. This value may then be used in a successive adjustment step for feedback control when driving the tool 100 according to the prescription data DATA.

Furthermore, other information may be exchanged as part of the information INFO, for example the strut ID for identifying the external fixation strut 200, or any other useful information.

As mentioned before, the tool 100 is configured to generate an alert when the date and/or time for the prescribed adjustment is reached, so that the patient may promptly couple said tool 100 the strut 200 when needed. However, the user may also postpone the application of the adjustment of the external fixation strut 200, for example by pressing one of the push buttons of the tool 100 when the alert is generated; in an embodiment, by pressing the bush button 1, the tool enters in the waiting state in which it waits to be coupled with the strut, while by pressing button 2 the correction is postponed.

More in particular, in an embodiment, when the correction is to be applied and the alert is generated, the controller 104 is programmed in such a way that that patient has the following options:

- immediately performing the entire correction;
- immediately performing a partial correction;
- snoozing the alert on the tool and postpone the correction, without performing any correction until the next adjustment is to be applied;
- snoozing the alert on the tool and postpone the correction, wherein the correction is applied at any time between the postponement operation and the next adjustment to be applied.

In case a correction is postponed, and no action is carried by the user until the next correction, said postponed correction will be automatically carried out during said next correction; in this case, the postponed correction will be added to the standard correction that should be applied in said next correction step. In an embodiment, when a postponement is selected (or when a partial correction is performed), the amount of the correction that is added in the next correction step is based the time elapsed from the last applied correction.

Furthermore, as mentioned before, according to an embodiment of the present disclosure, the controller 104 is configured to detect from the external unit 300 an update of the prescription data DATA and to download, either directly in its memory or indirectly via the user device 310, said update in order to substitute the previously downloaded prescription data with updated prescription data, so that the proper prescription may always be applied.

It is therefore clear that the automation of the operation of the tool 100 avoids errors of the patient improve the overall post-operative adjustment process, the patient being properly guided in all steps of the operation of the tool 100.

Figure 22:
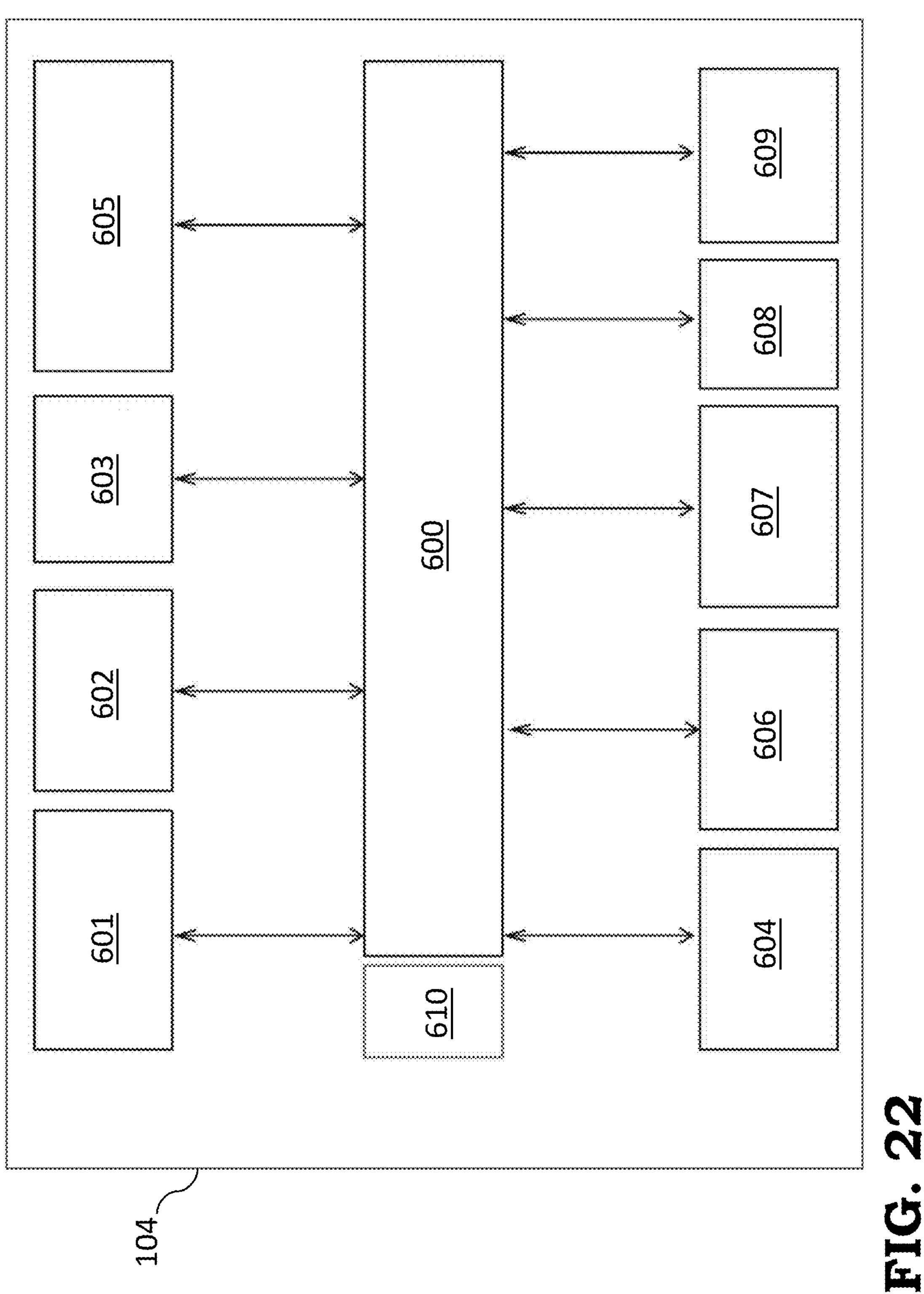
FIG. 22 is a block scheme of an exemplary architecture and connections according to embodiments of the present disclosure.

FIG. 22 is a block scheme of an exemplary architecture and connections according to embodiments of the present disclosure, wherein only data connections are shown for the sake of clarity.

In the shown example, the controller 104 of the tool 100 comprises a mainboard 600 which integrates the proper software modules for accomplishing the functionalities of said tool 100 that have been disclosed above.

A communication module 601 is configured for establishing a communication protocol with the struts 200. The communication between the tool 100 and the struts 200 may occur over a dc-coupled bus where both power and data are carried trough. In an embodiment, the communication is performed on a half-duplex serial bus where data is written or read to and from the struts 200.

Two main functions are performed by the communication module 601, namely writing an identification code to give identity ID to a brand new strut or to re-code a wrong-coded strut (and this operation is performed by the surgeon or any other suitable operator, as shown above), and reading said strut ID (which is performed both in surgeon and patient mode to read the ID of a strut after being coupled to the tool).

The communication module 601 is also configured to allow the reading of the strut length and position via the strut sensors.

The controller 104 is also programmed to implement a power management module 602 which is configured to manage all the power paths of the tool 100.

The controller 104 is also programmed to implement a USB data connection module 603, as well as a motor management/encoder module 604.

More in particular, the motor management/encoder module 604 is configured to ensure that the driving of the motor (which may be a brush motor) is done correctly. The hardware for driving the motor is apt to detect motor fault/over force, to set the speed, and to verify with a closed loop PID that the target speed is achieved. In particular, motor acceleration and deceleration ramps are implemented, and the operation is controlled by said closed loop PID by reading as feedback hall sensors.

Furthermore, a Buzzer/LED Ring module 605 is implemented as part of a safety module, said module being configured to inform the operator/patient when error, warning or notices occur, as shown above. The acoustic signals may have a predetermined pattern which may vary based on the circumstances, said acoustic signals being correlated with corresponding LED colors. The LED ring 120 is driven by a serial-concatenated bus (shift registers) which is apt to send color and intensity information to the LED. This operation is constantly performed to ensure the right color is always prompted respecting the alarm active on the system.

The software modules then comprise a keyboard management module 606 configured to recognize the pressure of the pushbuttons of the tool 100 and trigger the proper action.

The software modules then comprise an external flash and Ram module 607 and a display module 608.

Moreover, a connectivity module 609 is configured to enable connection to the external device 300, for example in order to check for new firmware updates, check for new prescriptions, upload on the cloud last life counters, logs or any data that have to be loaded, receive command to enable some specific modes of operation of the tool 100 (e.g., service mode or surgeon mode), and the like.

Finally, a safety module 610 is configured to ensure the proper and safe operation of the tool.

As part of the safety module, during treatment, the prescribed lengthening is monitored both from reading back data from the sensor of the strut and also from the rotation of the motor shaft. The right math is applied considering gearbox reduction rates between the motor of the tool 100 and the strut. If the value does not match within a certain threshold, the controller is configured to enter the tool 100 in a safe mode. In other words, the controller is configured to monitor the rotation of the output shaft 101 and to evaluate gearbox reduction rates between the motor 102 of the tool 100 and the strut 200.

The controller 104 may also be configured to generate interfaces I1-I23 on the display 116 of the tool 100, said interfaces I1-I23 being structured to show a respective operating status of said tool 100.

Figure 23D:
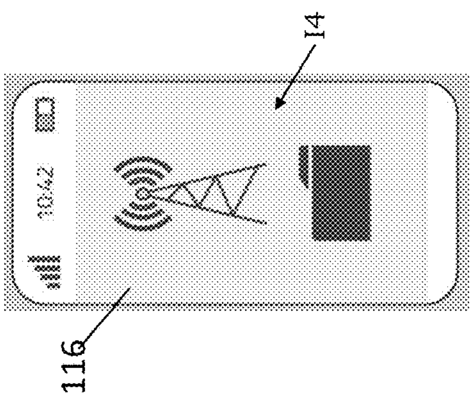
FIGS. 23A-23W show examples of interfaces displayed by a display of the tool according to embodiments of the present disclosure.
Figure 23C:
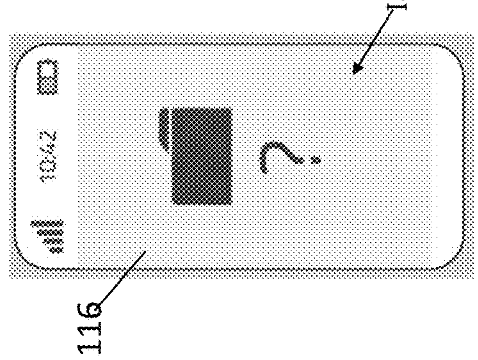
Figure 23B:
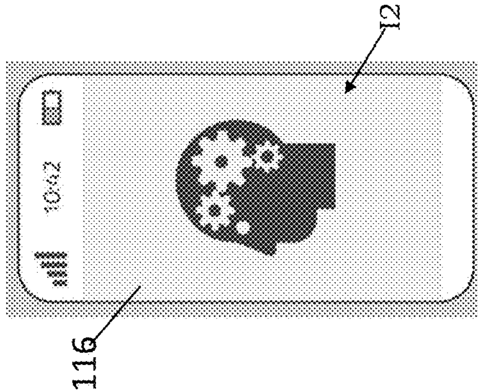
Figure 23A:
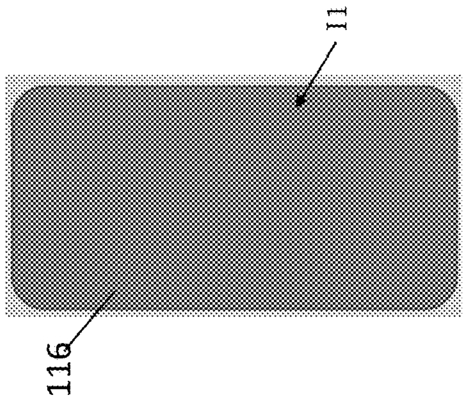
Figure 23H:
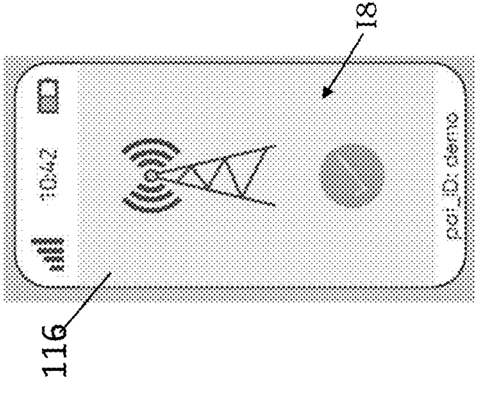
Figure 23G:
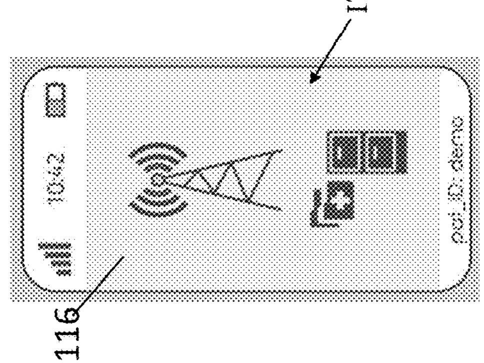
Figure 23F:
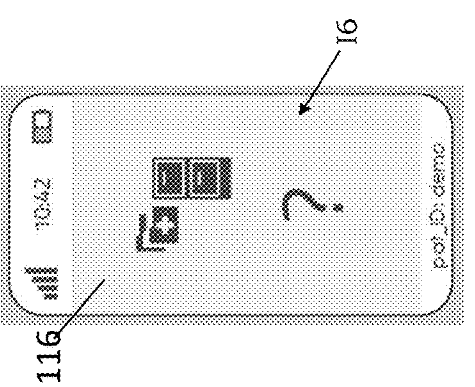
Figure 23E:
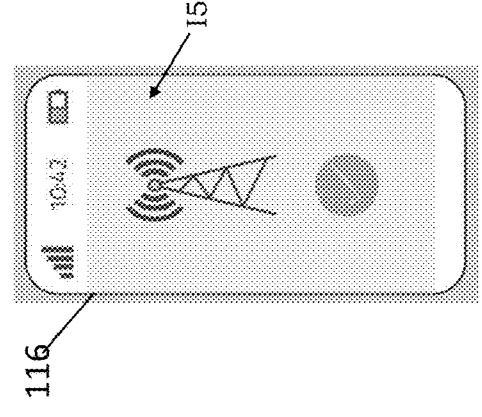
Figure 23L:
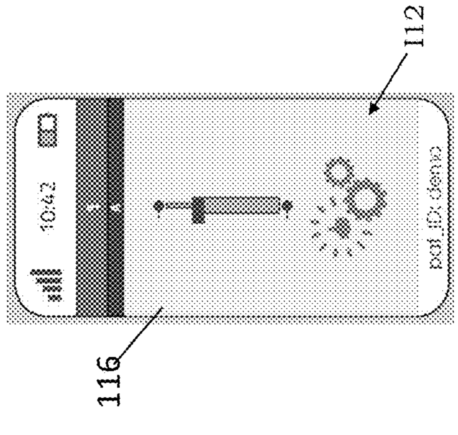
Figure 23K:
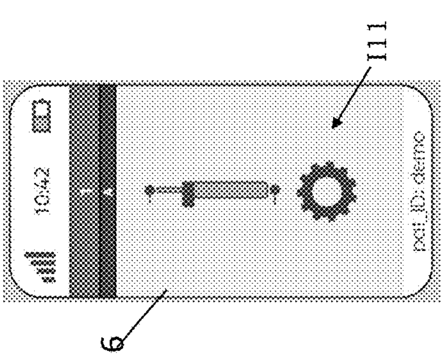
Figure 23K:
Figure 23J:
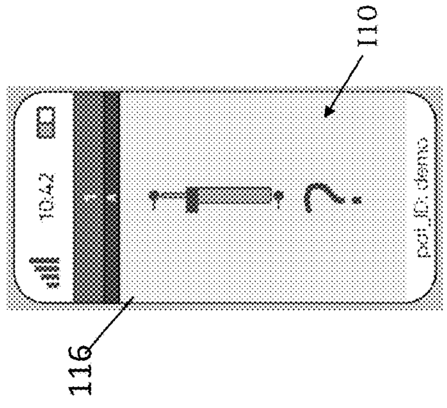
Figure 23I:
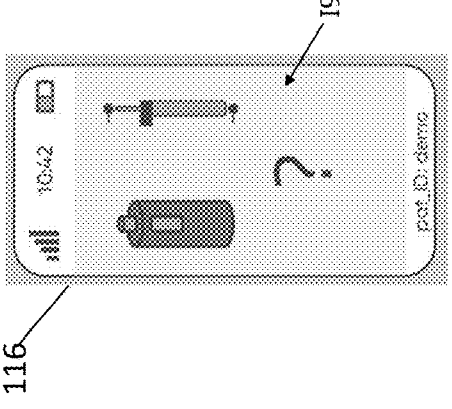
Figures 23M, 23N, 23O, 23P:
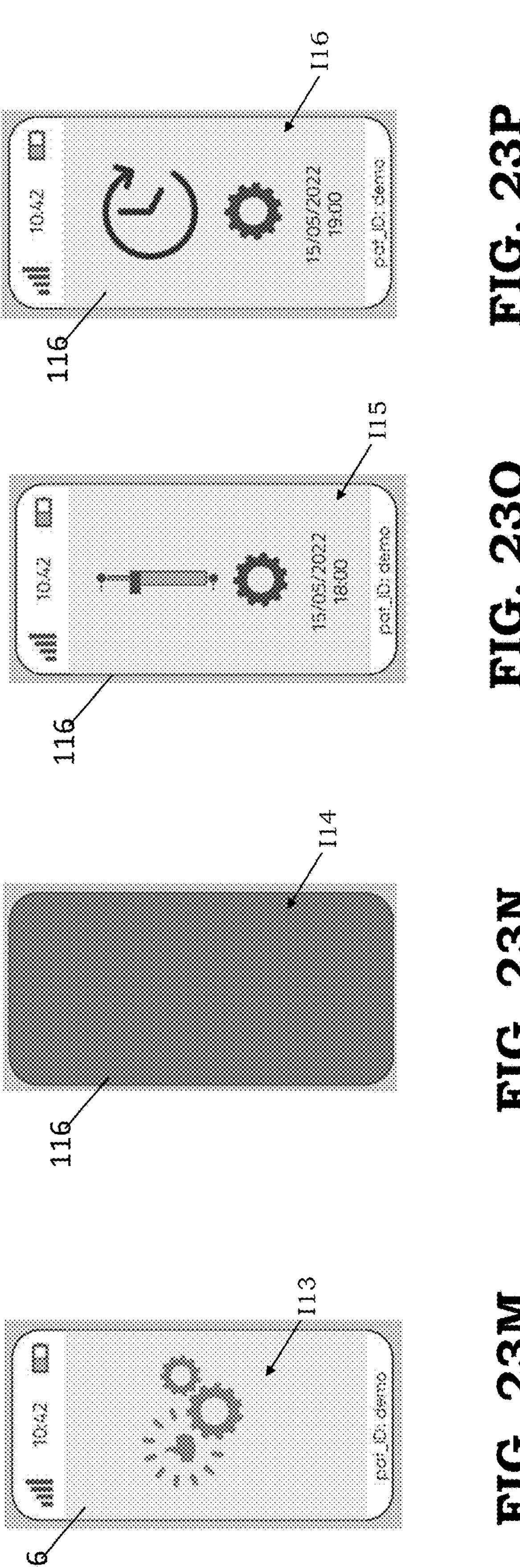
Figure 23T:
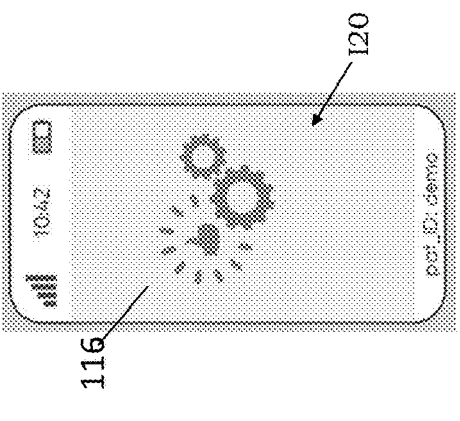
Figure 23T:
Figure 23T:
Figure 23T:
Figure 23S:
Figure 23S:
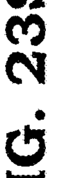
Figure 23S:
Figure 23R:
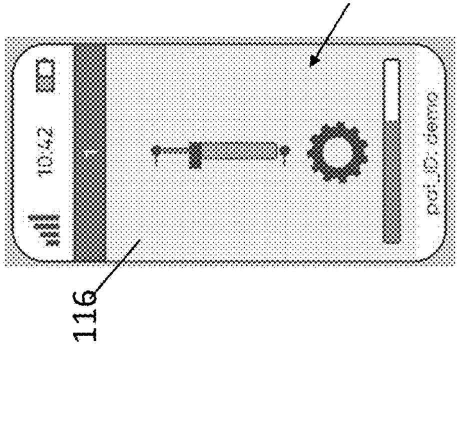
Figure 23R:
Figure 23Q:
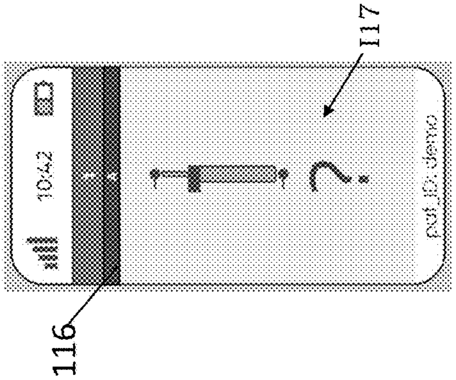
Figure 23Q:
Figure 23W:
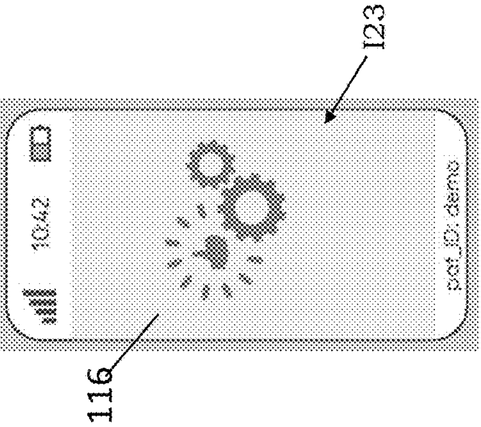

FIGS. 23A-23W show examples of the interfaces displayed in the display of the tool according to embodiments of the present disclosure. These figures will be discussed below in connection with FIGS. 24 and 25.

Figure 24:
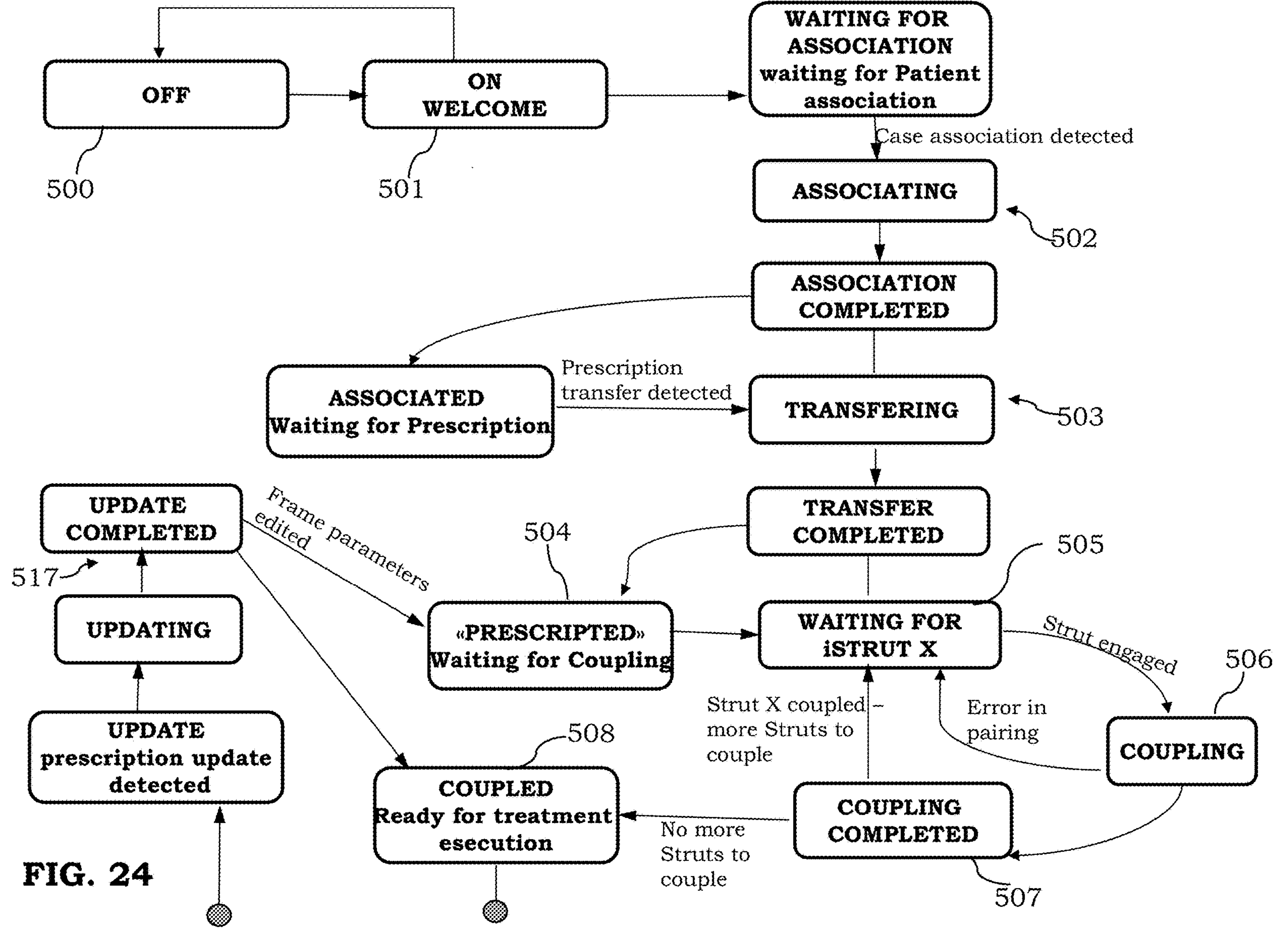
FIG. 24 is a top part of a flow chart showing operation of the tool according to embodiments of the present disclosure.
Figure 25:
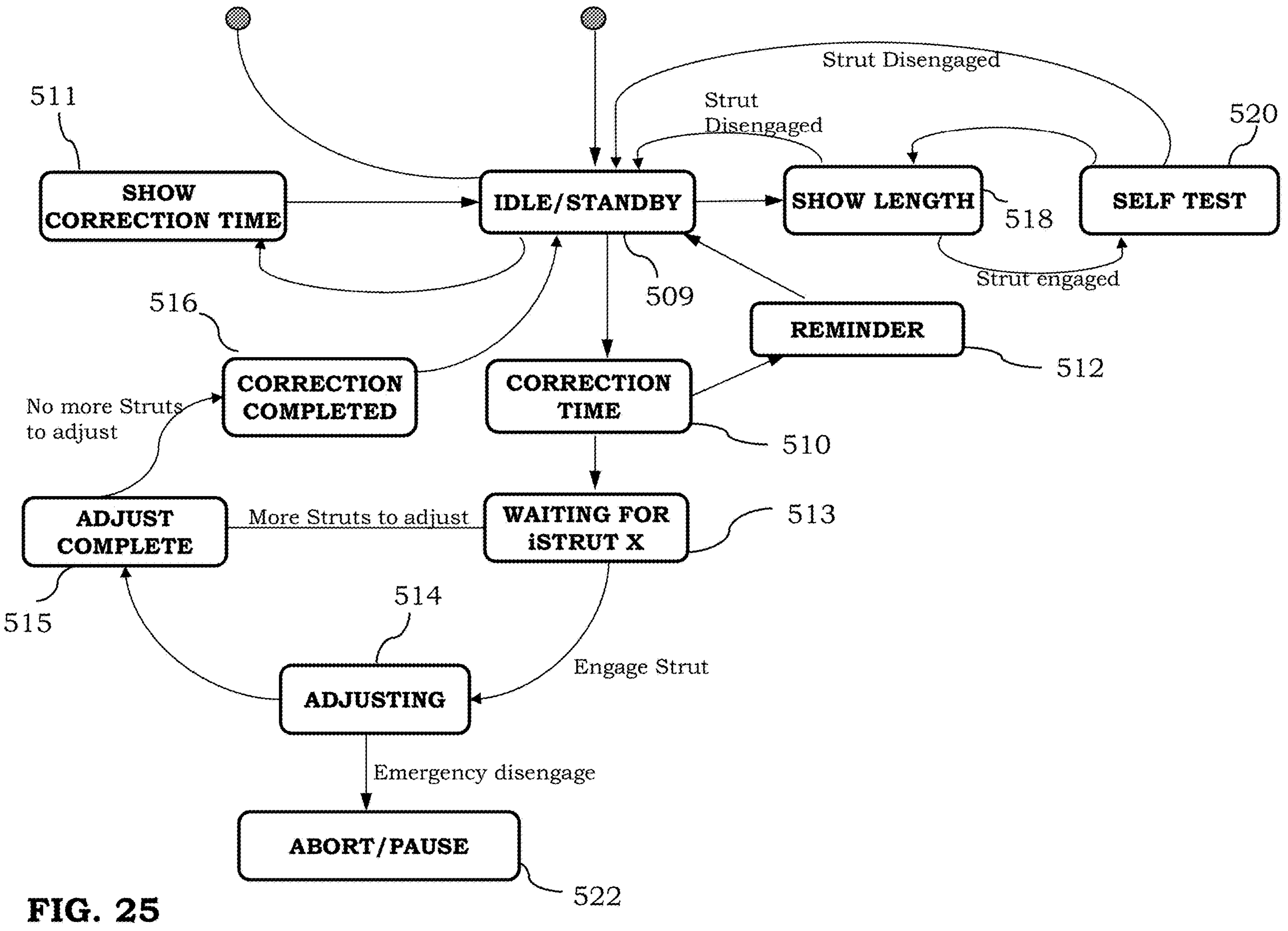
FIG. 25 is the bottom part of the flow chart of FIG. 24.

FIGS. 24 and 25 show a top and a bottom part of a flow diagram of the operation of tool 100 as disclosed above in connection with FIG. 21.

Summing up, the device can be turned from an off state 500 to an on state 501 by the user, for instance by pressing Button 1 or Button 2 for a given time. This may correspond to passage from interface I1 of FIG. 23A to interface I2 of FIG. 23B.

A similar user action may be demanded to return the device to the off state 500.

After a given time from being turned on, the device will be associated to a specific case 502, as represented by interfaces I3, I4, and I5 of FIGS. 23C, 23D, and 23E.

Then, after a command by the user, the device connects to the internet and retrieves from a dedicated portal the prescription data DATA for the patient's case 503 and, when this prescription treatment has been successfully transferred to the tool memory, informs the patient. This is represented by interfaces I6, I7, and I8 of FIGS. 23F, 23G, and 23H.

As mentioned before, there are multiple ways (e.g., GSM, BT, NFC, WiFi) direct-undirect to connect to the external unit 300 and the present disclosure is not limited by the communications means adopted.

After the prescription has been uploaded to the internal memory, the device is in a general waiting state 504 which may be signaled to the user via the display 116 and/or the annular LED indicator, as in interface I9 of FIG. 23I.

Upon a user command, for instance the pressure of Button 1, the device enters the coupling waiting state 505 and it will signal through the display 116 that it is ready to connect with a given strut, as shown in interface I10 of FIG. 23J.

In the coupling waiting state 505, the user is expected to mechanically couple the device to a strut 200 which, as previously discussed, also results in a data connection. When the tool is being coupled to a strut, the tool indicates it by interface I11 of FIG. 23K, and when the coupling is complete the tool indicates it by interface I12 of FIG. 23L.

When the data connection is performed 507, the device advises the user which may then couple the other struts 200 in a similar way.

Once all struts 200 have been correctly coupled, the device enters a coupled state 508, as represented in interface I13 of FIG. 23M.

Then, upon a command by the user, the device enters an idle state 509 (interface I14 of FIG. 23N) ready to signal when the prescribed correction date and/or time 510 is reached. In such a state, the user can interrogate the device—for instance, by pressing Button 1—which will then display the next correction time 511 (interface I15 of FIG. 23O).

Then, when the correction time 510 is eventually reached, the user may be advised via an audio and/or a visual signal that he/she is required to take action (as represented by interface I16 of FIG. 23P).

The user will then be granted the choice of either performing or postponing 512 the adjustment of the struts. Button 1 and Button 2 can be alternately employed to discriminate between the two choices.

If the user decides to perform the correction, the device will then guide the user toward engaging the struts 200 to be adjusted 513 (interface I17 of FIG. 23Q). Once the external fixation strut 200 is engaged, the device will automatically perform the adjustment in the adjustment step 514, and thereafter signal to the user that the adjustment is complete 515 (interfaces I18 and I19 of FIGS. 23R, and 23S).

If another strut is to be adjusted, steps 513-515 are repeated; otherwise, the device signals to the user that the correction is completed 516 (interface I20 of FIG. 23T), and returns to the idle state 509.

Figure 23V:
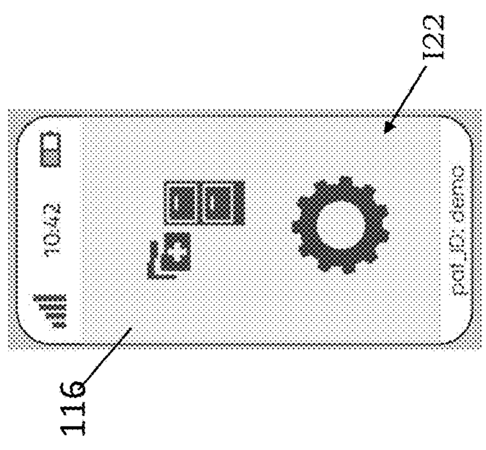
Figure 23U:
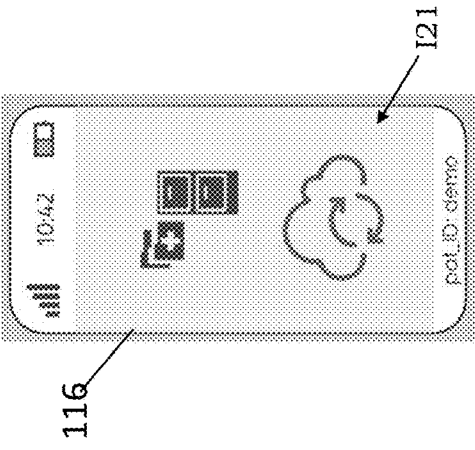

From the idle state 509, the device is also able to update the prescription 517 whenever a prescription update is detected (see interfaces I21, I22, and I23 of FIGS. 23U, 23V, and 23W). This update may be activated by pressure of a push button by the patient when the tool is in the idle state, or automatically done by the tool 100 by periodically checking for updates, for example by interacting with external unit 300.

In an embodiment, the patient or the surgeon can anytime (except during the correction phase) engage the tool 100 into a specific strut 200 in order to obtain the length thereof (state 518) and, with a pressure of one or more buttons, the controller 104 is configured to start a test on the strut 200 to verify that both mechanics and firmware of the strut are working as expected (state 520).

Moreover, in an embodiment, during the strut adjustment operation, the patient could disengage the tool 100 from the strut 200 as a safety mechanism in case he/she feels pain during the treatment (state 522).

It will be understood that particular embodiments described herein are shown by way of illustration and not as limitations of the disclosure. The principal features of this disclosure can be employed in various embodiments without departing from the scope of the disclosure. Those skilled in the art will recognize, or be able to ascertain using no more than routine experimentation, numerous equivalents to the specific devices and procedures described herein. Such equivalents are considered to be within the scope of this disclosure and are covered by the claims.

All publications and patent applications mentioned in the specification are indicative of the level of skill of those skilled in the art to which this disclosure pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Obviously, a person skilled in the art, in order to satisfy contingent and specific needs, can make various modifications and variations to the tool described above, all of which are within the scope of the disclosure as defined by the attached claims.

What is claimed is:

1. A tool for adjusting an external fixation strut, the external fixation strut having an adjustment mechanism for length adjustment and a second connecting portion, the tool comprising:

a first connecting portion adapted to perform data communication with the external fixation strut via the second connecting portion; and a controller which includes command instructions and, based on said command instructions, is configured to: download prescription data from an external unit, the prescription data relating to a determined patient's case and comprising instructions for performing an adjustment of the external fixation strut of the patient;

enter a waiting state in which it waits for coupling with the external fixation strut of the patient for communicating data therewith via the first connecting portion;

after the tool has been coupled with the external fixation strut, recognize a coupling state with the external fixation strut;

based on said coupling, communicate with the external fixation strut via the first connecting portion; and once said coupling is complete and data with the external fixation strut have been exchanged, wait for a date and/or time in which the prescribed adjustment is to be applied based on the prescription data, wherein, when the date and/or time when the strut adjustment is to be applied is reached, the controller is configured to enter a further waiting state in which it waits for a successive coupling for applying the prescribed adjustment to the external fixation strut, said successive coupling involving a mechanical engagement with the external fixation strut.

2. The tool of claim 1, wherein, during said coupling, the controller is configured to assign a strut ID to the external fixation strut.

3. The tool of claim 1, wherein the prescription data comprise a set of dates and/or times of successive adjustments to be applied to the external fixation strut and an extent of said adjustments, and wherein the controller is configured to generate an alert when the date and/or time of the prescribed adjustment is reached.

4. The tool of claim 1, wherein the state in which the controller waits for the date and/or time when the prescribed adjustment is to be applied is an idle state.

5. The tool of claim 1, wherein, after being mechanically engaged with the external fixation strut following the further waiting state, the controller is configured to apply the prescribed adjustment by driving tool means which are adapted to act on the adjustment mechanism of the external fixation strut.

6. The tool of claim 1, wherein, during the successive coupling, the controller is configured to retrieve from the external fixation strut information relating to the external fixation strut, wherein said information comprise at least a measurement indicative of a length of said external fixation strut, said length being used for feedback control for driving the tool according to the prescription data.

7. The tool of claim 6, wherein the controller is configured to retrieve the measurement indicative of the length of the external fixation strut from a sensor of the external fixation strut, said data passing through the first connecting portion.

8. The tool of claim 1, wherein the controller is configured to detect from the external unit an update of the prescription data and to download the update in order to substitute the previously downloaded prescription data with updated prescription data.

9. The tool of claim 1, wherein the controller is configured to postpone the application of the adjustment of the external fixation strut following a selection of the user.

10. The tool of claim 9, wherein, in case a postponement is selected by the user, the controller is configured to apply to the strut, during a next adjustment operation, the adjustment that has been postponed, an adjustment amount that is added during the next adjustment operation being based on an elapsed time from the last performed adjustment operation.

11. The tool of claim 1, comprising push buttons adapted to be engaged by a user in order to initiate or complete or select operating steps of the tool, and comprising means for communicating data with the external unit.

12. The tool of claim 1, wherein, after the coupling with one external fixation strut is completed, the controller is configured to check whether other external fixation struts are to be coupled by the tool and, if yes, to enter a waiting state in which it waits for the coupling with another external fixation strut of said other external fixation struts.

13. The tool of claim 12, wherein the controller is configured to generate an alert in case the patient engages the tool with a wrong strut.

14. The tool of claim 1, wherein the controller is configured to generate interfaces on a display of the tool, the interfaces being structured to show a respective operating status of said tool.

15. The tool of claim 1, comprising:

an output shaft; and a motor operable to rotate the output shaft, wherein the controller is configured to drive the motor according to the prescription data.

16. The tool of claim 15, wherein the controller is configured to monitor the rotation of the output shaft and to evaluate gearbox reduction rates between the motor of the tool and the strut.

17. The tool of claim 15, further comprising a first coupling portion solidly attached to the output shaft and adapted to releasably engage with a corresponding second coupling portion of the adjustment mechanism, thereby enabling torque transmission from the motor to the adjustment mechanism of the strut, wherein the first connecting portion is in electrical communication with the controller and is adapted to electrically connect with the second connecting portion when the first coupling portion is engaged with the second coupling portion, thereby enabling data transmission from the external fixation strut to the controller, and vice versa.

18. The tool of claim 17, wherein the tool further comprises a power supply, and wherein the electrical connection between the first connecting portion and the second connecting portion further enables power transmission to the external fixation strut.

19. A medical assembly comprising a tool according to claim 1; and one or more external fixation struts comprising:

an elongated body comprising at least a first shaft and a second shaft moveable with respect to each other to modify the length of said elongated body;

an adjustment mechanism for moving the second shaft with respect to the first shaft thereby modifying the length of the elongated body;

a second coupling portion of the adjustment mechanism adapted to releasably engage with a first coupling portion of the tool according to claim 1 to enable torque transmission;

at least one sensor adapted to perform at least a measurement which is indicative of the length of the elongated body; and a second connecting portion of the adjustment mechanism which is in electrical communication with the first connecting portion of the tool when the first coupling portion is engaged with the second coupling portion, and which is adapted to enable transmission of data from the sensor to the tool.

* * * * *